United States Patent [19]

Moseley et al.

[11] Patent Number: 6,080,740

[45] Date of Patent: Jun. 27, 2000

[54] SPIRO-KETAL DERIVATIVES AND THEIR USE AS THERAPEUTIC AGENTS

[75] Inventors: Jonathan David Moseley, Bristol; Christopher John Swain, Duxford, both of United Kingdom

[73] Assignee: Merck Sharp & Dohme Ltd., Hoddesdon, United Kingdom

[21] Appl. No.: 09/125,235

[22] PCT Filed: Feb. 13, 1997

[86] PCT No.: PCT/GB97/00404

§ 371 Date: Aug. 13, 1998

§ 102(e) Date: Aug. 13, 1998

[87] PCT Pub. No.: WO97/30056

PCT Pub. Date: Aug. 21, 1997

[30] Foreign Application Priority Data

May 15, 1996 [GB] United Kingdom ............... 9603136

[51] Int. Cl.$^7$ ................... A61K 31/537; C07D 498/10
[52] U.S. Cl. ........................... 514/230.8; 544/71
[58] Field of Search ............... 544/71; 514/230.8

[56] References Cited

U.S. PATENT DOCUMENTS

| 5,434,158 | 7/1995 | Shah ........................... 546/16 |
| 5,728,695 | 3/1998 | Harrison et al. ........................... 544/71 |

FOREIGN PATENT DOCUMENTS

| 0 577 394 | 1/1994 | European Pat. Off. . |
| WO 94/17045 | 8/1994 | WIPO . |
| WO 94/20500 | 9/1994 | WIPO . |
| WO 94/29309 | 12/1994 | WIPO . |
| WO 96/20197 | 7/1996 | WIPO . |

*Primary Examiner*—Mukund J. Shah
*Assistant Examiner*—V Balasubramanian
*Attorney, Agent, or Firm*—J. Eric Thies; David L. Rose

[57] ABSTRACT

The present invention is directed to spiro-ketal derivatives of the formula (I):

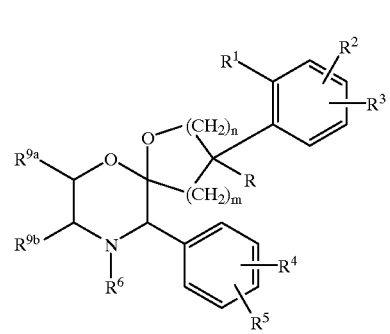

(wherein R, $R^1$, $R^2$, $R^3$, $R^4$, $R^5$, $R^6$, $R^{9a}$, $R^{9b}$, m and n are defined herein) which are tachykinin antagonists and are useful, for example, in the treatment or prevention of pain, inflammation, migraine, emesis and postherpetic neuralgia.

18 Claims, No Drawings

SPIRO-KETAL DERIVATIVES AND THEIR USE AS THERAPEUTIC AGENTS

CROSS REFERENCE TO RELATED APPLICATIONS

This application claims priority under 35 U.S.C. 371 from PCT/GB97/00404, filed Feb. 13, 1997, which claims priority from Great Britain Application No. 9603136.4, filed Feb. 15, 1996.

This invention relates to a class of spiroketal compounds which are useful as tachykinin antagonists. The present invention also relates to processes for their preparation, pharmaceutical compositions containing them, and to their use in therapy.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

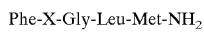

Phe-X-Gly-Leu-Met-NH$_2$

At present, there are three known mammalian tachykinins referred to as substance P, neurokin A (NKA, substance K, neuromedin L) and neurokinin B (NKB, neuromedin K) (for review see J. E. Maggio, *Peptides* (1985) 6(supp. 3), 237–242). The current nomenclature designates the three tachykinin receptors mediating the biological actions of substance P, NKA and NKB as the NK$_1$, NK$_2$ and NK$_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero, A. Giachetti, *J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem,* (1982) 25, 1009) and in arthritis [Levine et al *Science* (1984) 226, 547–549]. Tachykinins have also been implicated in gastrointestinal (GI) disorders and diseases of the GI tract such as inflammatory bowel disease [Mantyh et al *Neuroscience* (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, *Eur. J. Pharmacol.*, (1993) 250, R5–R6]. It is also hypothesised that there is a neurogenic mechanism for arthritis in which substance P may play a role [Kidd et al "A Neurogenic Mechanism for Symmetrical Arthritis" in *The Lancet*, Nov. 11, 1989 and Grönblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al, *J. Immunol.* (1988) 141(10), 3564–9 ]vasodilation, bronchospasm, reflex or neuronal control of the viscera [Mantyh et al, *PNAS* (1988) 85, 3235–9] and, possibility by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster *C.I.N.P. XVIIIth Congress, Jun.* 28–Jul. 2, 1992], and in disorders of bladder function such as bladder detrusor hyper-reflexia (*Lancet*, May 16, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European paten specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

European patent specification no. 0 577 394 (published Jan. 5, 1994) discloses morpholine and thiomorpholine tachykinin receptor antagonists of the general formula

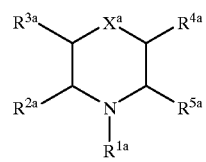

wherein $R^{1a}$ is a large variety of substituents;
$R^{2a}$ and $R^{3a}$ are inter alia hydrogen;
$R^{4a}$ is inter alia

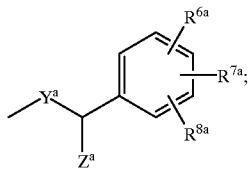

$R^{5a}$ is inter alia optionally substituted phenyl;
$R^{6a}$, $R^{7a}$ and $R^{8a}$ are a variety of substituents;
$X^a$ is O, S, SO or $SO_2$;
$Y^a$ is inter alia O; and
$Z^a$ is hydrogen or $C_{1-4}$alkyl.

We have now found a further class of non-peptides which are potent antagonists of tachykinins, especially of substance P.

The present invention provides compounds of the formula (I):

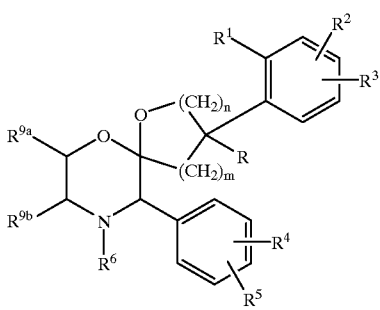

(I)

wherein

R represents hydroxy, $C_{1-6}$alkoxy, $C_{3-6}$alkenyloxy, $C_{3-6}$alkynyloxy, fluoro$C_{1-6}$alkoxy, $C_{3-7}$cycloalkoxy, $C_{3-7}$cycloalkyl$C_{1-4}$alkoxy, phenoxy, benzyloxy or halogen, wherein the phenyl moiety of said phenoxy or benzyloxy is optionally substituted by one, two or three substituents selected from $C_{1-6}$alkyl, $C_{1-6}$-alkoxy, halogen and trifluoromethyl;

$R^1$ represents hydrogen, halogen, $C_{1-6}$-alkyl, $C_{2-6}$-alkenyl, $C_{2-6}$alkynyl, $C_{3-7}$cycloalkyl, $C_{3-7}$cycloalkyl$C_{1-4}$alkyl, $C_{1-6}$alkoxy, fluoro$C_{1-6}$alkyl, fluoro$C_{1-6}$alkoxy, $C_{1-4}$alkyl substituted by a $C_{1-4}$alkoxy or hydroxy group, hydroxy, trimethylsilyl, nitro, CN, $SR^a$, $SOR^a$, $SO_2R^a$, $COR^a$, $CO_2R_a$, $CONR^aR^b$, $SO_2NR^aR^b$, or $OC_{1-4}$alkyl$NR^aR^b$, where $R^a$ and $R^b$ are each independently hydrogen or $C_{1-4}$alkyl;

$R^2$ and $R^3$ each independently represent hydrogen, halogen, $C_{1-6}$alkyl, $C_{1-6}$alkoxy substituted by $C_{1-4}$alkoxy or trifluoromethyl;

or R and $R^1$ may be joined such that $—R—R^1—$ is a linkage selected from $—O—CH_2—$ and $—O—CH_2CH_2—$;

or, where $R^1$ and $R^2$ are attached to adjacent carbon atoms, they may be joined such that, together with the carbon atoms to which they are attached, there is formed a 5- or 6-membered ring optionally containing 1 or 2 heteroatoms selected from oxygen, sulfur or nitrogen, or 1 or 2 groups selected from S(O), $S(O)_2$ and $NR^a$, which ring may also contain 1 or 2 double bonds, where $R^a$ is as previously defined;

$R^4$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, $C_{1-4}$alkyl substituted by a $C_{1-4}$alkoxy group, trifluoromethyl, nitro, CN, $SR^a$, $SOR^a$, $SO_2R^a$, $COR^a$, $CO_2R^a$, $CONR^aR_b$ where $R^a$ and $R^b$ are as previously defined;

$R^5$ represents hydrogen, halogen, $C_{1-6}$alkyl, $C_{1-6}$alkoxy substituted by $C_{1-4}$alkoxy or trifluoromethyl;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}$alkyl$R^{12}$, $CONR^{13}C_{2-6}$alkenyl, $CONR^{13}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula $—CH_2C{\equiv}CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 2 or 3 nitrogen atoms optionally substituted by $=O$ or $=S$ and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally containing an oxygen or sulphur ring atom, a group S(O) or $S(O)_2$or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^{9a}$ and $R^{9b}$ each independently represent hydrogen or $C_{1-4}$alkyl, or $R^{9a}$ and $R^{9b}$ are joined so, together with the carbon atoms to which they are attached, there is formed a $C_{5-7}$ ring;

$R^{12}$ represents $OR^a$, $CONR^aR^b$ or heteroaryl;

$R^{13}$ represents H or $C_{1-6}$alkyl;

m is zero, 1,2 or 3; and n is zero, 1, 2 or 3; with the proviso that the sum total of m and n is 2 or 3;

and pharmaceutically acceptable salts thereof.

A preferred class of compound of formula (I) is that wherein R represents hydroxy, $C_{1-3}$alkoxy, $C_{3-5}$alkenyloxy, phenoxy or halogen. Particularly preferred are those compounds where R represents hydroxy or $C_{1-3}$alkoxy, and especially those where R represents hydroxy or methoxy.

Where R represents a phenoxy or benzyloxy substituent the phenyl moiety of each substituent is preferably unsubstituted.

Where R represents a halogen atom, fluorine is preferred.

A preferred class of compound of formula (I) is that wherein $R^1$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, $C_{1-4}$alkyl substituted by a $C_{1-4}$alkoxy group, $OCF_3$, hydroxy, trifluoromethyl, trimethylsilyl, nitro, CN, $SR^a$, $SOR^a$, $SO_2R^a$, $COR^a$, $CO_2R^a$, $CONR^aR^b$ where $R^a$ and $R^b$ are each independently hydrogen or $C_{1-4}$alkyl; and $R^2$ and $R^3$ each independently represent hydrogen, halogen, $C_{1-6}$alkyl, $C_{1-6}$alkoxy substituted by a $C_{1-4}$alkoxy or trifluoromethyl.

Certain particularly apt compounds of the present invention include those wherein $R^1$ is hydrogen, $C_{1-4}$alkyl, $C_{1-4}$alkoxy, halogen, fluoro$C_{1-3}$alkyl or fluoro$C_{1-3}$alkoxy.

Most aptly $R^2$ is hydrogen, $C_{1-4}$alkyl, $C_{1-4}$alkoxy, halogen or $CF_3$.

Most aptly $R^3$ is hydrogen, fluorine, chlorine or $CF_3$.

Favourably $R^1$ is hydrogen, $C_{1-4}$alkyl, especially methyl, $C_{1-4}$alkoxy, especially methoxy, $OCF_3$ or $CF_3$.

Favourably $R^2$ is hydrogen, fluorine, chlorine, $C_{1-4}$alkyl or $CF_3$, especially hydrogen or $CF_3$.

Favourably $R^3$ is hydrogen.

Preferably $R^2$ is in the 5-position on the phenyl ring.

Most aptly $R^4$ is hydrogen.

Most aptly $R^5$ is hydrogen, fluorine, chlorine or $CF_3$.

Preferably $R^4$ is hydrogen and $R^5$ is 4-fluoro.

Most aptly $R^{9a}$ and $R^{9b}$ are each independently hydrogen or methyl.

Preferably $R^{9a}$ is hydrogen. Preferably $R^{9b}$ is hydrogen. Most preferably $R^{9a}$ and $R^{9b}$ are both hydrogen.

Preferably n is 1.

Preferably m is 1 or 2, especially 1.

Favourably $R^6$ is hydrogen, $C_{1-3}$alkyl, especially $CH_2$ and $CH(CH_3)$, substituted by phenyl wherein said phenyl ring is optionally substituted by $C_{1-3}$alkoxy (especially methoxy) or $CF_3$, or $R^6$ is a group of formula —$CH_2C\equiv CCH_2NR^7R^8$, or $R^6$ is $C_{1-3}$alkyl, in particular $CH_2$, $CH(CH_3)$ and $CH_2CH_2$ are especially $CH_2$, substituted by a 5-membered ring.

In particular, the 5-membered ring is a heterocyclic ring selected from:

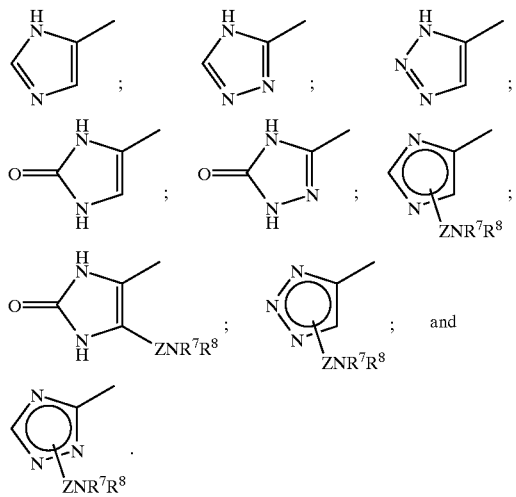

Particularly preferred heterocyclic rings are selected from:

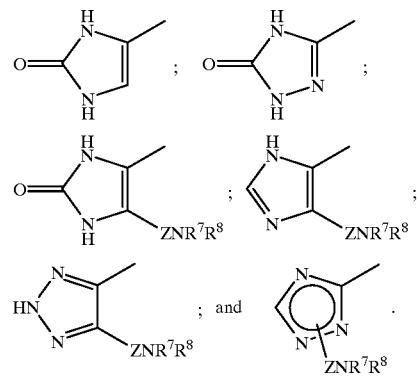

Most especially, the heterocyclic ring is selected from:

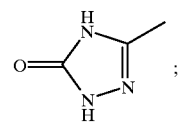

and

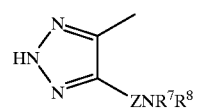

One favoured group of compounds of the present invention are of the formula (Ia) and pharmaceutically acceptable salts thereof:

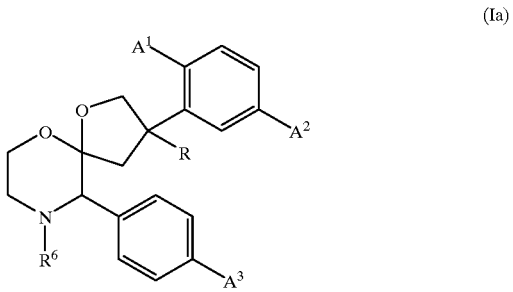

(Ia)

wherein R and $R^6$ are as defined in relation to formula (I);
$A^1$ is hydrogen, $C_{1-3}$alkyl, $C_{1-3}$alkoxy, halogen, fluoro$C_{1-3}$ alkyl or fluoro$C_{1-3}$alkoxy;
$A^2$ is hydrogen, halogen, $C_{1-4}$alkyl or fluoro$C_{1-3}$alkyl; and
$A^3$ is hydrogen or halogen.

In particular, $A^1$ is preferably hydrogen, methyl, methoxy, $OCF_3$ or $CF_3$.

In particular $A^2$ is hydrogen, fluorine or trifluoromethyl.

In particular $A^3$ is hydrogen or fluorine.

With respect to compounds of the formulae (I) and (Ia), Z (where present), may be a linear, branched or cyclic group. Favourably Z contains 1 to 4 carbon atoms and most favourably 1 to 2 carbon atoms. A particularly favourable group Z is $CH_2$.

With respect to compounds of the formulae (I) and (Ia), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{1-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

In the group $ZNR^7R^8$, Z is preferably $CH_2$ or $CH_2CH_2$, and especially $CH_2$.

The group $NR^7R^8$ preferably represents amino, methylamino, dimethylamino, diethylamino, azetidinyl, pyrrolidino or morpholino.

In particular, $NR^7R^8$ is preferably dimethylamino, azetidinyl or pyrrolidino, especially dimethylamino.

Where R and $R^1$ are joined such that —R—$R^1$—is a linkage, this is preferably —O—$CH_2$—, thereby forming a phthalan ring.

Where $R^1$ and $R^2$, together with the carbon atoms to which they are attached, form a 5- or 6-membered ring optionally containing 1 or 2 heteroatoms selected from oxygen, sulfur or nitrogen, or 1 or 2 groups selected from S(O), S(O)$_2$ and $NR^a$, and which ring may also contain 1 or 2 double bonds, it will be appreciated that the ring thus formed may be saturated, partially saturated or unsaturated. Thus, $R^1$ and $R^2$ may represent, for example, —$OCH_2CH_2CH_2$—, —$OCH_2CH_2O$—, —$OCH_2CH_2$—, —$OCH_2O$—, —$NR^aCH_2CH_2CH_2$—, —$NR^aCH_2CH_2$—, —$CH_2CH_2CH_2CH_2$—, —$CH_2CH_2CH_2$—, —CH=CH—CH=CH—, —O—CH=CH—, —$NR^a$—CH=CH—, —S—CH=CH—, —$NR^a$—CH=N, —O—CH=N—, —S—CH=N—, —N=CH—CH=CH—, —CH=N—CH=CH—. Particularly preferred linkages formed by $R^1$ and $R^2$ include, —$OCH_2CH_2CH_2$—, —$OCH_2CH_2O$—, —$OCH_2CH_2$—, —$OCH_2O$—, —$NR^aCH_2CH_2CH_2$— and —CH=CH—CH=CH—. In these examples, $R^a$ preferably represents a hydrogen atom.

As used herein, the term "alkyl" or "alkoxy" as a group or part of a group means that the group is straight or branched. Example of suitable alkyl groups include methyl, ethyl, n-propyl, i-propyl n-butyl, s-butyl and t-butyl. Examples of suitable alkoxy groups include methoxy, ethoxy, n-propoxy, i-propoxy, n-butoxy, s-butoxy and t-butoxy.

The cycloalky groups preferred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular, 1 to 3) hydrogen atoms have been replaced by a fluorine atom. Particularly preferred are fluoro$C_{1-3}$-alkyl and fluoro$C_{1-3}$alkoxy groups, for example, $CF_3$, $CH_2CH_2F$, $CH_2CHF_2CH_2CF_3$, $OCF_3$, $OCH_2CH_2F$, $OCH_2CHF_2$ or $OCH_2CF_3$, and most especially $CF_3$ and $OCF_3$.

When used herein the term halogen means fluorine, chlorine, bromine and iodine. The most apt halogens are fluorine and chlorine of which fluorine is preferred.

Specific compounds within the scope of this invention include:

(2R,3S,9R)-4-aza-4-benzyl-1,7-dioxa-3-(4-fluorophenyl)-9-hydroxy-9-phenyl-spiro[5.4]decane;
(2R,3S,9R)-4-aza-4-benzyl-1,7-dioxa-3-(4-fluorophenyl)-9-hydroxy-9-(2-methoxyphenyl)spiro[5.4]decane;
(2R,3S,9R)-4-aza-4-benzyl-1,7-dioxa-3-(4-fluorophenyl)-9-hydroxy-9-(2-(trifluoromethyl)phenyl)spiro[5.4]decane;
(2R,3S,9R)-4-aza-4-benzyl-1,7-dioxa-3-(4-fluorophenyl)-9-hydroxy-9-(2-methoxy-5-(trifluoromethyl)phenyl)spiro[5.4]decane;
(2R,3S,9R)-4-aza-4-benzyl-1,7-dioxa-3-(4-fluorophenyl)-9-hydroxy-9-(2-methoxy-5-(trifluoromethyl)phenyl)spiro[5.4]decane;
(2R,3S,9R)-4-aza-4-benzyl-1,7-dioxa-3-(4-fluorophenyl)-9-hydroxy-9-(2-(trifluoromethoxy)phenyl)spiro[5.4]decane;
(±)-(2R*,3S*,9R*)-4-aza-4-benzyl-1,7-dioxa-3-(4-fluorophenyl)-9-hydroxy-9-(2-methylphenyl)spiro[5.4]decane;
(2R,3S,9R)-4-aza-4-benzyl-1,7-dioxa-9-(2-ethylphenyl)-3-(4-fluorophenyl)-9-hydroxy-spiro[5.4]decane;
(2R,3S,9R)-4-aza-4-benzyl-9-(2-chlorophenyl)-1,7-dioxa-3-(4-fluorophenyl)-9-hydroxy-spiro[5.4]decane;
(2R,3S,9R)-4-aza-1,7-dioxa-3-(4-fluorophenyl)-9-hydroxy-9-phenylspiro[5.4]decane;
(2R,3S,9R)-4-aza-1,7-dioxa-3-(4-fluorophenyl)-9-hydroxy-9-(2-methoxyphenyl)spiro[5.4]decane;
(2R,3S,9R)-4-aza-1,7-dioxa-3-(4-fluorophenyl)-9-hydroxy-9-(2-(trifluoromethyl)phenyl)spiro[5.4]decane;
(2R,3S,9R)-4-aza-1,7-dioxa-3-(4-fluorophenyl)-9-hydroxy-9-(2-methoxy-5-(trifluoromethyl)phenyl)spiro[5.4]decane;
(2R,3S,9R)-4-aza-1,7-dioxa-3-(4-fluorophenyl)-9-hydroxy-9-(2-methoxy-5-(trifluoromethyl)phenyl)spiro[5.4]decane;
(2R,3S,9R)-4-aza-1,7-dioxa-3-(4-fluorophenyl)-9-hydroxy-9-(2-(trifluoromethoxyl)phenyl)spiro[5.4]decane;
(±)-(2R*,3S*,9R*)-4-aza-1,7-dioxa-3-(4-fluorophenyl)-9-hydroxy-9-(2-methylphenyl)spiro[5.4]decane;
(2R,3S,9R)-4-aza-4-(2,3-dihydro-3-oxo-1,2,4-triazol-5-yl)methyl-1,7-dioxa-3-(4-fluorophenyl)-9-hydroxy-9-(2-methoxyphenyl)spiro[5.4]decane;
(2R,3S,9R)-4-aza-4-(2,3-dihydro-3-oxo-1,2,4-triazol-5-yl)methyl-1,7-dioxa-3-(4-fluorophenyl)-9-hydroxy-9-(2-(trifluoromethyl)phenyl)-spiro[5.4]decane;
(2R,3S,9R)-4-aza-4-(4-(N,N-dimethylamino)-but-2-ynyl)-1,7-dioxa-3-(4-fluorphenyl)-9-hydroxy-9-(2-methoxy-5-(trifluoromethyl)phenyl)-spiro[5.4]decane;
(2R,3S,9R)-4-aza-4-(5-(N,N-dimethylaminomethyl)-1,2,3-triazol-4-yl)methyl-1,7-dioxa-3-(4-fluorophenyl)-9-hydroxy-9-(2-methoxy-5-(trifluoromethyl)phenyl)spiro[5.4]decane;

(2R,3S,9R)-4-aza-1,7-dioxa-3-(4-fluorophenyl)-9-hydroxy-4-(1(S)-phenylethyl)-9-(2-(trifluoromethyl)phenyl)spiro[5.4]decane;

(2R,3S,9R)-4-aza-1,7-dioxa-3-(4-fluorophenyl)-9-hydroxy-4-(1(R)-phenylethyl)-9-(2-(trifluoromethyl)phenyl)spiro[5.4]decane;

(2R,3S,9R)-4-aza-1,7-dioxa-3-(4-fluorophenyl)-9-hydroxy-4-((2-(trifluoromethyl)phenyl)methyl)-9-(2-(trifluoromethyl)phenyl)-spiro[5.4]decane;

(±)-(2R*,3S*,9R*)-4-aza-1,7-dioxa-3-(4-fluorophenyl)-9-methoxy-9-phenyl-spiro[5.4]decane;

(2R,3S,9R)-4-aza-4-benzyl-1,7-dioxa-3-(4-fluorophenyl)-9-methoxy-9-(2-methoxyphenyl)spiro[5.4]decane;

(2R,3S,9R)-4-aza-4-benzyl-1,7-dioxa-3-(4-fluorophenyl)-9-methoxy-9-(2-(trifluoromethyl)phenyl)spiro[5.4]decane;

(2R,3S,9R)-4-aza-4-benzyl-1,7-dioxa-3-(4-fluorophenyl)-9-methoxy-9-(2-methoxy-5-(trifluoromethyl)phenyl)spiro[5.4]decane;

(±)-(2R*,3S*,9R*)-4-aza-4-benzyl-1,7-dioxa-3-(4-fluorophenyl)-9-methoxy-9-(2-methylphenyl)spiro[5.4]decane;

(2R,3S,9R)-4-aza-4-benzyl-1,7-dioxa-9-(2-ethylphenyl)-3-(4-fluorophenyl)-9-methoxy-spiro[5.4]decane;

(2R,3S,9R)-4-aza-4-benzyl-9-(2-chlorophenyl)-1,7-dioxa-3-(4-fluorophenyl)-9-methoxy-spiro[5.4]decane;

(±)-(2R*,3S*,9R*)-4-aza-1,7-dioxa-3-(4-fluorophenyl)-9-methoxy-9-phenyl-spiro[5.4]decane;

(2R,3S,9R)-4-aza-1,7-dioxa-3-(4-fluorophenyl)-9-methoxy-9-(2-methoxyphenyl)spiro[5.4]decane;

(2R,3S,9R)-4-aza-1,7-dioxa-3-(4-fluorophenyl)-9-methoxy-9-(2-(trifluoromethyl)phenyl)spiro[5.4]decane;

(2R,3S,9R)-4-aza-1,7-dioxa-3-(4-fluorophenyl)-9-methoxy-9-(2-methoxy-5-(trifluoromethyl)phenyl)spiro[5.4]decane;

(2R,3S,9R)-4-aza-1,7-dioxa-3-(4-fluorophenyl)-9-methoxy-9-(2-methylphenyl)spiro[5.4]decane;

(2R,3S,9R)-4-aza-1,7-dioxa-9-(2-ethylphenyl)-3-(4-fluorophenyl)-9-methoxy-spiro[5.4]decane;

(2R,3S,9R)-4-aza-4-(5-(N,N-dimethylaminomethyl)-1,2,3-triazol-4-yl)methyl-1,7-dioxa-3-(4-fluorophenyl)-9-methoxy-9(2-methoxy-5-(trifluoromethyl)phenyl)spiro[5.4]decane;

(2R,3S,9R)-4-aza-4-(5-(N,N-dimethylaminomethyl)-1,2,3-tetrazol-4-yl)methyl-1,7-dioxa-3-(4-fluorophenyl)-9-methoxy-9-(2-(trifluoromethyl)phenyl)spiro[5.4]decane;

(2R,3S,9R)-4-aza-1,7-dioxa-3-(4-fluorophenyl)-9-methoxy-4-(1-(S)-phenylethyl)-9-(2-methoxy-5-(trifluoromethyl)phenyl)spiro[5.4]decane;

(2R,3S,9R)-4-aza-1,7-dioxa-3-(4-fluorophenyl)-9-methoxy-4-(1-(R)-phenylethyl)-9-(2-methoxy-5-(trifluoromethyl)phenyl)spiro[5.4]decane;

(2R,3S,9R)-4-aza-1,7-dioxa-3-(4-fluorophenyl)-9-methoxy-9-(2-methoxy-5-(trifluoromethyl)phenyl)-4-((2-(trifluoromethyl)phenyl)methyl)-spiro[5.4]decane;

(2R,3S,9R)-4-aza-1,7-dioxa-3-(4-fluorophenyl)-9-methoxy-9-(2-methoxy-5-(trifluoromethyl)phenyl)-4-((3-(trifluoromethyl)phenyl)methyl)-spiro[5.4]decane;

(2R,3S,9R)-4-aza-1,7-dioxa-3-(4-fluorophenyl)-9-methoxy-9-(2-methoxy-5-(trifluoromethyl)phenyl)-4-((4-(trifluoromethyl)phenyl)methyl)-spiro[5.4]decane;

(2R,3S,9R)-4-aza-1,7-dioxa-3-(4-fluorophenyl)-9-methoxy-4-((2-methoxyphenyl)methyl)-9-(2-methoxy-5-(trifluoromethyl)phenyl)spiro[5.4]decane;

(2R,3S,9R)-9-allyloxy-4-aza-4-benzyl-1,7-dioxa-3-(4-fluorophenyl)-9-phenyl-spiro[5.4]decane;

(2R,3S,9R)-4-aza-4-benzyl-1,7-dioxa-3-(4-fluorophenyl)-9-phenyl-9-(phenylmethoyloxy)spiro[5.4]decane;

(2R,3S,9R)-4-aza-1,7-dioxa-3-(4-fluorophenyl)-9-phenyl-9-propyloxy-spiro[5.4]decane;

(2R,3S,9R)-4-aza-1,7-dioxa-9-fluoro-3-(4-fluorophenyl)-9-phenyl-spiro[5.4]decane;

(2R,3S,9R)-4-aza-1,7-dioxa-9-fluoro-3-(4-fluorophenyl)-9-phenylspiro[5.4]decane;

(2R,3S,9R)-4-aza-4-benzyl-1,7-dioxa-3-(4-fluorophenyl)-9-hydroxy-9-(2-(hydroxymethyl)phenyl)spiro[5.4]decane;

[2'R-[2'α(S*),4'α]]-3"-(4-fluorophenyl)-4"-(phenylmethyl)dispiro-[isobenzofuran-1(3H),4'(5'H)-furan-2'(3H),2"-morpholine];

[2'R-[2'α(S*),4'α]]-3"-(4-fluorophenyl)dispiro[isobenzofuran-1(3H),4'(5'H)-furan-2'(3H),2"-morpholine];

and pharmaceutically acceptable salts thereof.

In a further aspect of the present invention, the compounds of formula (I) will preferably be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) will have the preferred stereochemistry of the 2-, 3- and 9-positions that is possessed by the compound of Example 1 (2R,3S,9R). Thus for example as shown in formula (Ib)

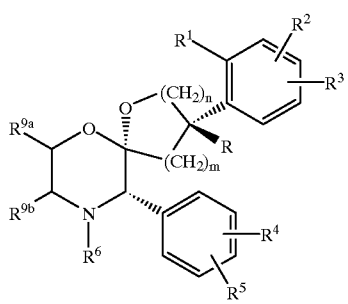

(Ib)

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nubulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives. sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways diseases, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.,* (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D$_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

It will be appreciated that for the treatment or prevention of pain or nociception, a compound of the present invention may be used in conjunction with other analgesics, such as acetaminophen (paracetamol), aspirin and other NSAIDs and in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan, gepirone and ipsaperone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A), compounds of formula (I) wherein R is a hydroxy group, may be prepared from a compound of formula (II)

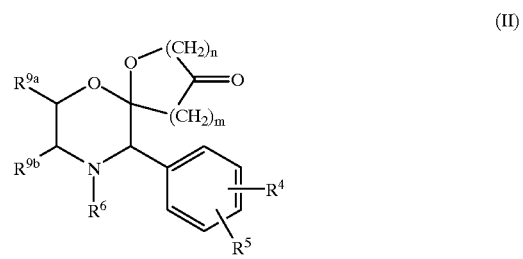

(II)

wherein $R^4$, $R^5$, $R^6$, $R^{9a}$, $R^{9b}$, m and n are as defined in relation to formula (I) by reaction with a Grignard or organolithium compound of formula (IIIA) or (IIIB)

(IIIA)

-continued (IIIB)

wherein $R^1$, $R^2$ and $R^3$ are as defined in relation to formula (I) and Hal is a halogen atom, for example, chlorine, bromine or iodine, especially a bromine atom.

Both reactions are effected under conventional conditions, for instance, in a suitable solvent such as an ether, e.g. tetrahydrofuran, at a temperature between −90° and −60° C., with subsequent quenching using, for example, saturated ammonium chloride solution.

According to a general process (B), compounds of formula (I) wherein R is a group selected from $C_{1-6}$alkoxy, $C_{3-6}$alkenyloxy, $C_{3-6}$alkynyloxy, fluoro$C_{1-6}$alkoxy, $C_{3-7}$cycloalkoxy, $C_{3-7}$cycloalkyl$C_{1-4}$alkoxy, phenoxy or benzyloxy, may be prepared from the corresponding compound of formula (I) in which R is a hydroxy group, hereinafter referred to as compounds of formula (IV)

(IV)

by reaction with a suitable alkyl halide, alkenyl halide, alkynyl halide, fluoroalkyl halide, cycloalkyl halide, cycloalkylalkyl halide, phenyl halide or benzyl halide.

The reaction is conveniently effected in the presence of a base such as an alkali metal halide, for example, sodium hydride in a suitable solvent, for example an organic solvent such as N,N-dimethylformamide, preferably at a temperature between 10° C. and 50° C., conveniently at room temperature.

According to another general process (C), compounds of formula (I) wherein R is a halogen atom, may be prepared from a corresponding compound of formula (IV) by reaction with a suitable halogenating reagent. Thus, for example, compounds wherein R is fluorine may be prepared by reaction with diethylaminosulfur trifluoride, the reaction being effected in a suitable organic solvent such as a halogenated hydrocarbon, for example, dichloromethane, at a temperature between −90° C. and −0° C., for example, at about −78° C.

According to another general process (D), compounds of formula (I) wherein $R^6$ is H may be prepared from the corresponding compound of formula (I) in which $R^6$ is benzyl group. The reaction may be effected, for instance, under conventional conditions of catalytic hydrogenation using a palladium or platinum catalyst or an oxide thereof, the reaction being effected in a suitable solvent such as an alcohol, for example, methanol, conveniently at room temperature.

According to a further general process (E), compounds of formula (I) may be prepared from the corresponding compound of formula (I) in which $R^6$ is H, hereinafter referred to as compounds of formula (V)

(V)

wherein R, $R^1$, $R^2$, $R^3$, $R^4$, $R^5$, $R^{9a}$, $R^{9b}$, m and n are as defined in relation to formula (I), by reaction with a compound of formula (VI):

$$LG—R^{6a} \qquad (VI)$$

wherein $R^{6a}$ is a group of the formula $R^6$ as defined in relation to formula (I) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in a conventional manner, for example in an organic solvent such as dimethylformamide in the presence of an acid acceptor such as potassium carbonate.

According to another process (F), compounds of formula (I) wherein $R^6$ represents a 1,2,3-triazol-4-ylmethyl group substituted by $CH_2NR^7R^8$, may be prepared by reaction of a compound of formula (VII)

(VII)

with an amine of formula $NHR^7R^8$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to a further process (G), compounds of formula (I) wherein $R^6$ represents a $C_{1-6}$alkyl group which is substituted by an unsubstituted or substituted 1,2,4-triazolyl group, may be prepared by reaction of an intermediate of formula (V) with a compound of formula (VIII)

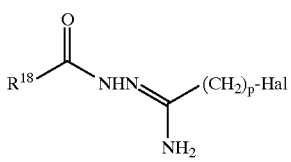

(VIII)

wherein Hal is a halogen atom, for example, bromine, chlorine or iodine, p is an integer from 1 to 6 $R^{18}$ is H, $CONH_2$ or $OCH_3$ (which is converted to an oxo substituent under the reaction conditions), in the presence of a base, followed where necessary by conversion to a compound of formula (I), for example, by reduction of the $CONH_2$ group to $CH_2NH_2$.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group $CONH_2$ is lithium aluminum hydride, used at between −10° C. and room temperature.

According to a further process (H), compounds of formula (I) may also be prepared from other compounds of formula (I) using suitable interconversion procedures. In particular, interconversion processes may be used to vary the group $R^6$. For example, compounds of formula (I) wherein $R^6$ is other than H may be prepared from the corresponding compounds of formula (I) wherein $R^6$ is H by reaction with a reagent suitable to introduce the group $R^6$, for example, compounds of formula (I) wherein $R^6$ is $COR^a$ may be prepared from compounds of formula (I) wherein $R^6$ is H by, for example, reaction with an appropriate acid anhydride.

Compounds of formula (I) wherein $R^6$ is $C_{1-6}$alkyl may be prepared from corresponding compounds of formula (I) wherein $R^6$ is $COR^a$ by reduction using, for example, borane or a borohydride such as sodium cyanoborohydride.

Compounds of formula (I) wherein $R^6$ is $C_{1-6}$alkyl substituted by $CONR^aR^b$ may be prepared from corresponding compounds of formula (I) wherein $R^6$ is $C_{1-6}$alkyl substituted by $CO_2R^a$ by treatment with ammonia or an amine of formula $NR^aR^b$.

Compounds of formula (I) wherein $R^6$ is $C_{1-6}$alkyl substituted by 5-oxadiazolyl may be prepared from compounds of formula (I) wherein $R^6$ is $C_{1-6}$alkyl substituted by $CO_2R^a$, where $R^a$ represents $C_{1-6}$alkyl, by reaction with a compound of formula (IX)

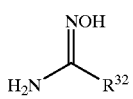

(IX)

wherein $R^{32}$ represents H or a suitable substituent, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

Compounds of formula (I) wherein $R^6$ is $C_{1-6}$alkyl substituted by thiazolyl may be prepared from compounds of formula (I) wherein $R^6$ is $C_{1-6}$alkyl substituted by $CSNH_2$ by reaction with a compound of formula Hal—$CH_2C(O)$—$R^{60}$, where Hal is a halogen atom, such as bromine, chlorine or iodine, and $R^{60}$ represents H or a suitable substituent.

Compounds of formula (I) wherein $R^6$ is $C_{1-6}$alkyl substituted by thioxotriazolyl may be prepared from compounds of formula (I) wherein $R^6$ is $C_{1-6}$alkyl substituted by $CONHNH_2$ by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

According to another general process (J), compounds of formula (I) wherein $R^6$ represents the group —$CH_2C\equiv CCH_2NR^7R^8$, may be prepared from a compound of formula (X)

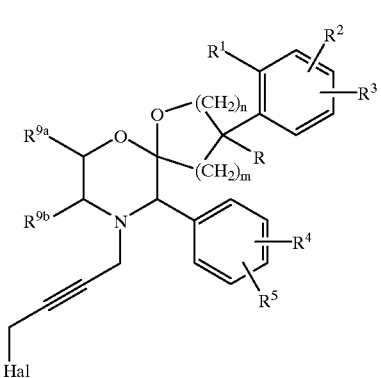

(X)

wherein Hal is a halogen atom such as chlorine, bromine or iodine, by reaction with an amine of formula $HNR^7R^8$ in the presence of a base.

Suitable bases of use in the reaction include alkali metal carbonates such as, for example, potassium carbonate. The reaction is conveniently effected in an organic solvent such as, for example, N,N-dimethylformamide, conveniently at room temperature.

Intermediates of formula (II) may be prepared by the oxidation of a compound of formula (XI)

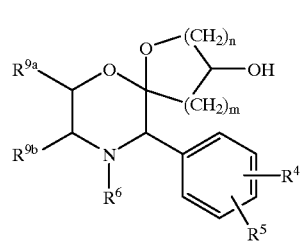

(XI)

under conventional conditions for the oxidation of a secondary alcohol. Particularly preferred are the conditions of the Swern oxidation, i.e. dimethylsulfoxide and oxalyl chloride, which reaction is conveniently effected in a halogenated hydrocarbon such as dichloromethane, preferably at a temperature below −70° C.

Compounds of formula (XI) may be prepared from a compound of formula (XII)

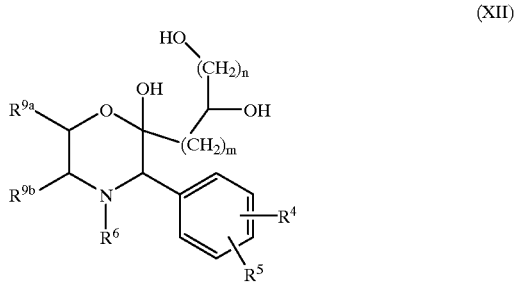

(XII)

by an acid catalysed intramolecular cyclisation reaction.

Suitable acids of use in the reaction include mineral acids such as, for example, hydrochloric acid. The reaction is conveniently effected in a suitable organic solvent, such as an alcohol, for example, methanol, at elevated temperature, for example, at the reflux temperature of the chosen solvent.

Intermediates of formula (XII) wherein n is 1 may be prepared by the hydroxylation of a compound of formula (XIII):

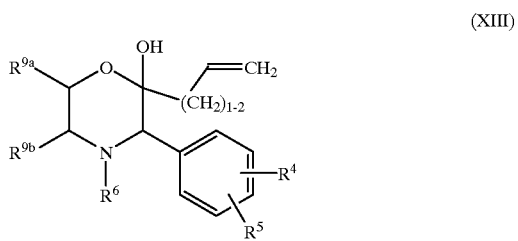

(XIII)

using conventional methodology, for instance, using osmium tetroxide and N-methylmorpholine-N-oxide, preferably in an inert solvent such as an ether, for example, tetrahydrofuran, or an alcohol, for example, isobutyl alcohol, or water or a mixture thereof, conveniently at room temperature.

Compounds of formula (XIII) may be prepared by the reaction of a compound of formula (XIV):

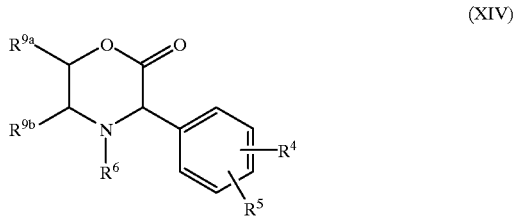

(XIV)

with a compound of formula (XV):

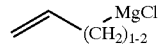

(XV)

using conventional Grignard conditions, for example, the reaction being effected in a solvent such as an ether, e.g. tetrahydrofuran, at reduced temperature, for example, at −78° C.

Compounds of formula (XIV) may be prepared by methods described in European Patent Specification No. 0 577 394-A, or by analogous methods.

Compounds of formula (XV) are known compounds.

Intermediates of formula (VII) may be prepared from a compound of formula (X) by reaction with an azide, for example, sodium azide in a suitable solvent such as dimethylsulphoxide at or below room temperature.

Compounds of formula (X) may be prepared by a dropwise addition of an intermediate of formula (V) to a dihaloacetylene of formula Hal—$CH_2$—C≡C—$CH_2$—Hal where each Hal is independently chlorine, bromine or iodine, especially chlorine. The reaction is conveniently effected in a suitable solvent such as dimethylformamide in the presence of a base such as potassium carbonate.

Compounds of formula (VIII) may be prepared as described in J. Med. Chem., (1984) 27, 849.

For compounds wherein $R^6$ is a $C_{1-6}$alkyl group substituted by a 5-membered heterocycle which in turn is substituted by a $ZNR^7R^8$ group where Z is $CH_2$, certain favoured compounds of formula (I) may be prepared from a corresponding compound with a hydrogen atom in place of the $ZNR^7R^8$. Thus, for example a compound of the formula (I) wherein $R^6$ is an imidazolinone group carrying a $CH_2NR^7R^8$ moiety may be prepared from a corresponding compound lacking the $CH_2NR^7R^8$ moiety by reaction with formaldehyde and an amine $NHR^7R^8$ under conventional Mannich reaction conditions, for example in methanol with heating. If desired a pre-formed reagent such as $R^7R^8N^+$=$CH_2.I^-$ may be employed and a tertiary amine such as triethylamine used as acid acceptor.

Alternatively a compound of formula (I) wherein $R^6$ is a $C_{1-6}$alkyl group substituted by an imidazolinone group may be reacted with paraformaldehyde and an amine for example a secondary amine such as pyrrolidine or morpholine to give a compound wherein the imidazolinone ring is substituted by $CH_2NR^7R^8$ where $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety, where $R^c$ is as previously defined.

This reaction may be performed in a conventional manner, for instance, in a suitable solvent such as an alcohol, for example, methanol at an elevated temperature up to the boiling point of the solvent.

A further alternative method for the preparation of certain compounds of formula (I) involves the reaction of an intermediate of formula (V) as defined above with one of the compounds of formula (XVI):

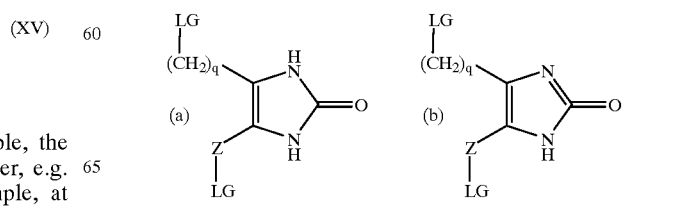

(XVI)

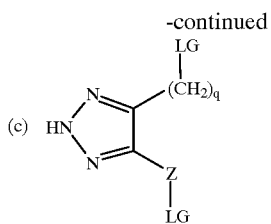

(c)

wherein each LG, which may be the same or different, is a leaving group, such as an alkyl- or arylsulphonyloxy group (e.g. mesylate or tosylate) or, in particular, a halogen atom, (e.g. bromine, chlorine or iodine), q is an integer from 1 to 6 and Z are as defined in formula (I), followed by reaction of the resultant compound with an amine $NHR^7R^8$ to complete the $ZNR^7R^8$ moiety.

This reaction is conveniently effected in an organic solvent such as dimethylformamide in the presence of an acid acceptor such as potassium carbonate.

It will be appreciated that, where necessary, reactive groups may be protected, thus for example, the NH groups of an imidazolinone of formula (XIIa) may be protected by any suitable amine protecting group such as an acetyl group.

It will be further appreciated that similar methodology may be used for the preparation of compounds where the group $ZNR^7R^8$ is absent.

Compounds of formulae (IIIA) and (IIIB) are either known compounds or may be prepared from a corresponding compound of formula (XVII)

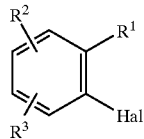

(XVII)

wherein Hal is a halogen atom, for example, chlorine, bromine or iodine, especially bromine, using conventional conditions for the synthesis of Grignard reagents or organolithium reagents.

An alternative convenient method for the preparation of compounds of formula (II), in which n is 1, is that illustrated by Scheme A, below, or using methods analogous thereto:

Scheme A

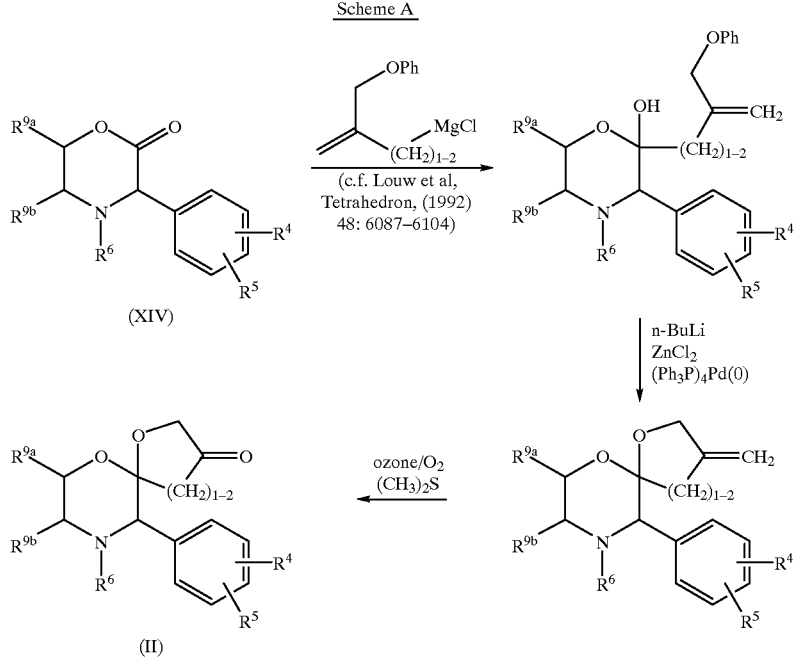

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (VI) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic*

Chemistry, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

Further methods suitable for adaptation to the preparation of the spiroketal compounds of the present invention are described by F. Perron and K. F. Albizati in *Chem. Rev.*, (1989) 89, 1617–1661.

The exemplified compounds of this invention were tested by the methods set out at pages 36 to 39 of International Patent Specification No. WO 93/01165. The compounds or, in the case of prodrugs, the parent compounds, were found to be active with $IC_{50}$ at the $NK_1$ receptor of less than 1 μM on said test method.

For the avoidance of doubt, the nomenclature adhered to throughout this specification is based upon the following structures:

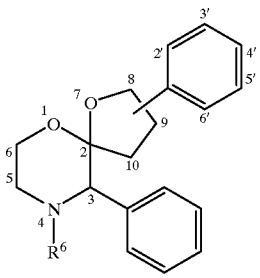

and

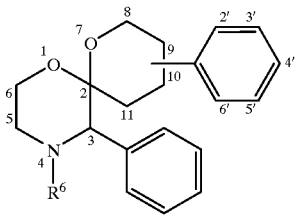

The following non-limiting Examples serve to illustrate the preparation of compounds of the present invention:

DESCRIPTION 1

(2R,3S)-4-Benzyl-3-(4-fluorophenyl)-2-hydroxy-2-(prop-2-enyl)morpholine (3S)-4-Benzyl-3-(4-fluorophenyl)-2-morpholinone (see International Patent Specification No. WO 95/18124) (13.6 g, 47.6 mmol) was dissolved in anhydrous tetrahydrofuran (200 ml) and cooled to below −70° C. under an inert atmosphere. Allyl magnesium chloride (26.2 ml of a 2.0M solution in tetrahydrofuran; 52.4 mmol) was added dropwise over 15 minutes, maintaining the temperature below −70° C. After 30 minutes, the reaction was quenched by the addition of a saturated solution of ammonium chloride and allowed to warm to room temperature. The resulting suspension was extracted with ethyl acetate (3×100 ml), and the combined organic extracts dried ($MgSO_4$) and concentrated in vacuo to yield the title compound in ~3:1 mixture of the lactols as a light yellow oil (15.3 g, 98%), which was used without further purification. m/z ($ES^+$) 328 (M+1, 22%), 310 (M—OH, 61), 269 (100).

DESCRIPTION 2

(2R,3S)-4-Benzyl-2-(2,3-dihydroxy)propyl-3-(4-fluorophenyl)-2-hydroxymorpholine

The alkene of Description 1 (18.9 g, 57.7 mmol) was stirred with osmium tetroxide (0.2 g, 0.8 mmol) and N-methylmorpholine N-oxide (7.78 g, 66.4 mmol) in a solution of tetrahydrofuran (200 ml), 2-methyl-2-propanol (120 ml) and water (14 ml) for 3 days at room temperature. The resulting black solution was diluted with ethyl acetate (200 ml), water (200 ml) and saturated brine (100 ml), separated and the organic fraction dried ($MgSO_4$) and concentrated in vacuo. The resulting black oil (26 g) was purified by flash silica gel chromatography eluting with 50–100% ethyl acetate in hexane to yield the title compound as a mixture of isomers as a white foam (15.9 g, 76%). Analysis Found: C, 65.22; H, 6.74; N, 3.68. $C_{20}H_{24}FNO_4.0.5 H_2O$ requires C, 64.84; H, 6.82; N, 3.78% m/z ($ES^+$) 362 (M+1, 18%), 344 (M—OH, 100).

DESCRIPTIONS 3A and 3B (2R,3S,9RS)-4-Aza-4-benzyl-1,7-dioxa-3-(4-fluorophenyl)-9-hydroxyspiro[5,4]decane; and (2S, 3S,9RS)-4-Aza-4-benzyl-1,7-dioxa-3-(4-fluorophenyl)-9-hydroxyspiro[5,4]decane The mixture of triols of Description 2 (15.0 g, 41.5 mmol) was dissolved in hydrochloric acid (200 ml, 6 M), and methanol (100 ml) and heated at reflux for 5 hours. The cooled solution was basified with 4N sodium hydroxide solution and extracted with ethyl acetate (3×200 ml). The combined organic extracts were dried ($MgSO_4$) and concentrated in vacuo. The resulting black oil (18 g) was purified by flash silica gel chromatography eluting with 33–66% ethyl acetate in hexane to yield the title compounds as pairs of diasteromers. The less polar isomer pair (Description 3A), was obtained as an orange gum (7.1 g, 50%). $R_f$ 0.37 (50% ethyl acetate/hexane). $^1$H NMR (360 MHz, $CDCl_3$) δ 0.42 (~½ H, d, J=10.4 Hz)*, 1.69 (½ H, dd, J=13.5, 5.5 Hz), 1.86 (½ H, d, J=14.6 Hz), 1.96 (½ H, d, J=13.6 Hz), 2.15 (½ H, dd, J=14.6, 6.4 Hz), 2.30 (1 H, dt, J=12.0, 3.6 Hz), 2.76 (1 H, d, J=13.1 Hz), 2.79 (1 H, d, J=13.2 Hz), 3.11 (~½ H, d, J=11.2 Hz)*, 3.34 (1 H, d, J=14.2 Hz), 3.35–3.71 (3 H, m), 3.91 (½ H, dd, J=9.7, 3.6 Hz), 3.98–4.24 (2½ H, m), 7.01 (2×½ H, t, J=8.8 Hz), 7.08 (2×½ H, t, J=8.7 Hz), 7.18–7.29 (5 H, m), 7.54 and 7.63 (2 H, 2×br s) (* exchanges in $D_2O$); m/z ($ES^+$) 344 (M×1, 100%).

The more polar isomer pair (Description 3B) was obtained as an orange glass (4.3 g, 30%). $R_f$ 0.25 (50% ethyl acetate/hexane). $^1$H NMR (360 MHz, $CDCl_3$) δ 0.83 (⅔ H, br d)*, 1.64 (⅓ H, dd, J=14.0, 5.7 Hz), 1.87 (⅔ H, d, J=14.6 Hz), 2.02 (⅓ H, J=14.0 Hz), 2.15 (⅔ H, dd, J=14.6, 6.6 Hz), 2.32–2.41 (1 H, m), 2.74–2.82 (1 H, m), 3.03 (⅓ H, d, J=11.0 Hz)*, 3.14 (⅔ H, d, J=13.7 Hz), 3.17 (⅓ H, d, J=13.7 Hz), 3.50 (⅓ H, d, J=13.6 Hz), 3.59 (⅔ H, d, J=13.7 Hz), 3.66–4.16 (5⅓ H, m), 4.33 (⅔ H, br s), 7.00–7.09 (2H total, m), 7.21–7.31 (5 H, m), 7.41–7.52 (2 H total, m) (* exchanges in $D_2O$); m/z ($ES^+$) 344 (M+1, 100%).

DESCRIPTION 4

(2R,3S)-4-Aza-4-benzyl-1,7-dioxa-3-(4-fluorophenyl)-9-oxospiro[5,4]decane

Anhydrous dimethylsulphoxide (3.4 ml, 47.8 mmol) dissolved in dichloromethane (10 ml) was added dropwise over 10 minutes to a solution of oxalyl chloride (2.0 ml, 22.9 mmol) dissolved in anhydrous dichloromethane (200 ml) cooled in below −70° C. The temperature was maintained below −60° C. during the addition and the solution stirred for a further 15 minutes at below −70° C. The alcohol isomer pair A (Description 3A) (6.57 g, 19.1 mmol) dissolved in dichloromethane (40 ml) was added dropwise over 10 minutes, maintaining the temperature below −70° C., and then stirred at this temperature for one hour. Triethylamine (13.3 ml, 95.5 mmol) was added dropwise over 10 minutes, and the reaction allowed to warm to room temperature. The resulting mixture was washed with dilute sodium bicarbonate solution (0.2M) and water (200 ml) and the organic fraction dried (MgSO$_4$) and concentrated in vacuo (7.9 g). The crude product was purified by flash silica gel chromatography eluting with 14–20% ethyl acetate in hexane to yield the title compound as a pale yellow glass which solidified to a buff coloured solid on standing (5.2 g, 80%). Analysis Found: C, 70.29; H, 5.83; H, 4.02. C$_{20}$H$_{20}$FNO$_3$ requires C, 70.37; H, 5.91; N, 4.10%. [α]$^{22}_D$=+125.6 (c=1.04, CH$_2$Cl$_2$); $^1$H NMR (360 MHz, CDCl$_3$) δ 2.31 (2 H, d, J=3.0 Hz), 2.35 (1 H, dt, J=12.0, 3.5 Hz), 2.80 (1 H, d, J=12.9 Hz), 2.83 (1 H, br d, J=11.0 Hz), 3.52 (1 H, s), 3.59 (1 H, dq, J=10.1, 1.6 Hz), 3.68 (1 H, d, J=13.2 Hz), 3.88 (1 H, d, J=16.6 Hz), 4.03 (1 H, d, J=16.6 Hz), 4.18 (1 H, dt, J=11.7, 2.5 Hz), 7.05 (1 H, t, J=8.7 Hz), 7.19–7.32 (5 H, m), 7.58 (2 H, br s); m/z (ES$^+$) 342 (M+1, 100%).

DESCRIPTION 5

(2R,3S,9R)-4-Aza-4-(4-chlorobut-2-ynyl)-1,7-dioxa-3-(4-fluorophenyl)-9-hydroxy-9-(2-methoxy-5-(trifluoromethyl)phenyl)spiro[5,4]decane A solution of 1,4-dichlorobutyne (196 μl, 2.0 mmol) in DMF (30 ml) and potassium carbonate (709 mg, 5.13 mmol) was heated to 60° C. The morpholine of Example 12 (731 mg, 1.71 mmol) as a solution in DMF (10 ml) was added dropwise over 5 minutes and the reaction stirred for 3 hours. The cooled reaction mixture was diluted with water (100 ml), extracted with ether (3×40 ml), dried (MgSO$_4$) and concentrated to an orange oil which was purified by flash silica gel chromatography eluting with 2:1 to 1:1 hexane-:ethyl acetate to yield the title compound as a yellow oil (326 mg, 37%). m/z (ES$^+$) 514/516 (3:1, M+1, 100%).

DESCRIPTION 6

(2R,3S,9R)-4-Aza-4-(4-azidobut-2-ynyl)-1,7-dioxa-3-(4-fluorophenyl)-9-hydroxy-9-(2-methoxy-5-(trifluoromethyl)phenyl)spiro[5,4]decane Sodium azide (97 mg, 1.48 mmol) was added to a solution of the chloride of Description 5 (255 mg, 0.49 mmol) dissolved in DMSO (10 ml) and stirred for 18 hours. The reaction mixture was diluted with saturated ammonium chloride solution (100 ml), extracted with ethyl acetate (3×40 ml), dried (MgSO$_4$) and concentrated to a crude oil which was purified by flash silica gel chromatography eluting with 4:1 hexane:ethyl acetate to yield the title compound as an oil (232 mg, 91%); m/z (ES$^+$) 521 (M+1, 100%).

DESCRIPTION 7

(2R,3S,9R)-4-Aza-4-(4-chlorobut-2-ynyl)-1,7-dioxa-3-(4-fluorophenyl)-9-methoxy-(2-methoxy-5-(trifluoromethyl)phenyl)spiro[5,4]decane The title compound was prepared from the morpholine of Example 32 according to the method of Description 5 to yield a glass (137 mg, 44%). $^1$H NMR (360 MHz, CDCl$_3$) δ 2.25 (1 H, d, J=14.0), 2.53 (1 H, d, J=14.0), 2.78 (1 H, dd, J=11.4, 1.4), 2.93–3.01 (1 H, m), 2.98 (3 H, s), 3.07 (1 H, dt, J=17.4, 1.9), 3.19 (1 H, dt, J=17.5, 1.8), 3.63 (1 H, s), 3.67 (3 H, s), 3.76 (1 H, dd, J=11.5, 2.7), 3.90 (1 H, d, J=9.8), 4.17 (2 H, s), 4.39 (1 H, dt, J=11.8, 2.8), 4.44 (1 H, d, J=9.8), 6.81 (1 H, d, J=8.6), 6.87 (2 H, t, J=8.1), 7.22 (1 H, d, J=2.1), 7.44 (~2 H, br s), 7.45 (1 H, dd, J=8.7, 1.9); m/z (ES$^+$) 528/530 (3:1, M+1, 100%).

DESCRIPTION 8

(2R,3S,9R)-4-Aza-4(4-azidobut-2-ynyl)-1,7-dioxa-3-(4-fluorophenyl)-9-methoxy-9-(2-methoxy-5-(trifluoromethyl)phenyl)spiro[5,4]decane The title compound was prepared from the chloride of Description 7 according to the method of Description 6 to yield an oil (104 mg, 76%). m/z (ES$^+$) 535 (M+1, 100%).

DESCRIPTION 9

(2R,3S,9R)-4-Aza-4-(4-chlorobut-2-ynyl)-1,7-dioxa-3-(4-fluorophenyl)-9-methoxy-9-(2-(trifluoromethyl)phenyl)spiro[5,4]decane The title compound was prepared from the morpholine of Example 31 according to the method of Description 5 to yield an oil (193 mg, 84%).

DESCRIPTION 10

(2R,3S,9R)-4-Aza-4-(4-azidobut-2ynyl)-1,7-dioxa-3-(4-fluorophenyl)-9-methoxy-9-(2-(trifluoromethyl)phenyl)spiro[5,4]decane The title compound was prepared from the chloride of Description 9 according to the method of Description 6 to yield an oil (166 mg, 86%).

DESCRIPTION 11

2-Bromobenzyl triisopropylsilyl ether

Triisopropylsilyl chloride (8.0 ml, 46.0 mmol) was added dropwise to a solution of 2-bromobenzyl alcohol (7.0 g, 39.6 mmol) and imidazole (5.1 g, 75.0 mmol) in DMF (25 ml) and the resulting solution stirred at 20° C for 18 hours. The reaction mixture was diluted with water (400 ml) and extracted with ethyl acetate (3×75 ml). The combined organic extracts was washed with saturated brine (1×75 ml), dried (MgSO$_4$) and concentrated to yield the title compound as a clear oil (10.2 g, 78%). $^1$H NMR (250 MHz, CDCl$_3$) δ 1.05–1.24 (21 H, m), 4.82 (2 H, s), 7.11 (1 H, dt, J=7.5, 1.2), 7.34 (1 H, t, J=7.6), 7.48 (1 H, dd, J=7.9, 1.1), 7.63 (1 H, d, J=6.7).

DESCRIPTION 12

(2R,3S,9R)-4-Aza-benzyl-1,7-dioxa-3-(4-fluorophenyl)-9-hydroxy-9-(2-((triisopropylsilyloxy)methyl)phenyl)spiro[5,4]decane Tert-butyl lithium (1.69 ml, 1.7M solution in pentane, 2.87 mmol) was added dropwise to a solution of the bromide of Description 11 (2.0 g, 5.85 mmol) in ether (5 ml) cooled to −78° C., the temperature rising to −30° C. during the addition. The benzyl ketone of Description 4 (1.0 g, 2.83 mmol) as a solution in ether (3 ml) was added dropwise over 20 minutes and the resulting solution allowed to warm to 20° C. over 1½ hours. The reaction was quenched by the addition of saturated ammonium chloride solution, extracted with ethyl acetate (3×40 ml) and the combined organic extracts washed with saturated brine (1×40 ml), dried (MgSO$_4$) and concentrated to a yellow oil. The crude concentrate was purified by flash silica gel chromatography eluting with 19:1 hexane:ethyl acetate to yield the title compound as an oil contaminated with an equal mass of unreacted benzyl ketone (350 mg total) and was used without further purification in Example 47; m/z (ES$^+$) 606 (M+1, 100%).

EXAMPLE 1

(2R,3S,9R)-4-Aza-4-benzyl-1,7-dioxa-3-(4-fluorophenyl)-9-hydroxy-9-phenyl-spiro[5,4]decane Phenyl magnesium bromide (750 μl of a 3.0M solution in ether, 2.25 mmol) was added dropwise over 10 minutes to an ice cold solution of the benzyl ketone of Description 4 (512 mg, 1.50 mmol) in tetrahydrofuran (10 ml). The reaction mixture was allowed to warm to 20° C. over 2 hours before being quenched with saturated ammonium chloride solution (15 ml), extracted with ethyl acetate (3×15 ml), dried (MgSO$_4$) and concentrated to dryness. The resulting crude gum (852 mg) was purified by flash silica gel chromatography eluting with 7:3 hexane:ether to yield the title compound as an off-white foam (232 mg, 37%). Analysis Found: C, 74.77; H, 6.19; N, 3.21. $C_{26}H_{26}FNO_3$ requires C, 74.43; H, 6.26; N, 3.34%. $^1$H NMR (360 MHz, CDCl$_3$) δ 2.18 (1 H, d, J=13.5), 2.23 (1 H, d, J=13.6), 2.36 (1 H, dt, J=12.1, 3.3), 2.81 (2 H, t, J=12.1), 3.54 (1 H, s), 3.54 (1 H, s), 3.66 (3 H, m), 4.20 (2 H, m), 4.34 (1 H, dt, J=11.4, 3.0), 7.05–7.12 (4 H, m), 7.19–7.26 (8 H, m), 7.62 (2 H, br s); m/z (ES$^+$) 420 (M+1, 100%).

EXAMPLE 2

(2R,3S,9R)-4-Aza-4-benzyl-1,7-dioxa-3-(4-fluorophenyl)-9-hydroxy-9-(2-methoxyphenyl)spiro[5,4]decane n-Butyl lithium (1.03 ml, 1.6M in hexanes, 1.65 mmol) was added dropwise over 2 minutes to a solution of 2-bromoanisole (210 μl, 1.70 mmol) in tetrahydrofuran (5 ml) cooled to below −70° C. The solution was maintained at this temperature and stirred for 40 minutes before the benzyl ketone of Description 4 (0.50 g, 1.46 mmol) as a solution in tetrahydrofuran (5 ml) was added dropwise over 10 minutes maintaining the temperature below −70° C. The solution was stirred for 10 minutes before warming to 20° C. over 1 hour and quenched with a saturated ammonium chloride solution (20 ml). The resulting suspension was extracted with ethyl acetate (3×15 ml), dried (MgSO$_4$) and concentrated to a black gum (0.64 g), which was further purified by flash silica chromatography eluting with 20% ethyl acetate in hexane. The title compound was obtained as a pale yellow gum (0.21 g, 32%) which solidified on standing. $^1$H NMR (250 MHz, CDCl$_3$) δ 2.03 (1 H, d, J=13.0), 2.34 (1 H, dt, J=11.9, 3.5), 2.61 (1 H, d, J=13.0), 2.77 (1 H, d, J=13.2), 2.82 (1 H, br d, J=13.5), 3.37 (3 H, s), 3.55 (1 H, s), 3.62–3.70 (2 H, m), 4.13 (2 H, d, J=1.4), 4.34 (1 H, dt, J=12.0, 2.5), 4.60 (1 H, s), 6.73 (1 H, d, J=8.2), 6.90 (1 H, dt, J=7.5, 1.1), 7.05 (1 H, t, J=8.8), 7.16–7.28 (7 H, m), 7.52 (1 H, dd, J=7.8, 1.8), 7.62 (2 H, br s); m/z (ES$^+$) 450 (M+1, 100%), (M—OH, 20).

EXAMPLE 3

(2R,3S,9R)-4-Aza-4-benzyl-1,7-dioxa-3-(4-fluorophenyl)-9-hydroxy-9-(2-(trifluoromethyl)phenyl)spiro[5,4]decane N-Butyl lithium (3.5 ml of a 1.6M solution in hexanes, 5.6 mmol) was added dropwise over 15 minutes to a solution of 2-(trifluoromethyl)-iodobenzene (1.47 g, 5.4 mmol) in ether (15 ml) cooled to −10° C. After stirring for 1 hour, a 1.2M solution of tributoxyzirconium chloride in ether (4.7 ml, 5.6 mmol) (*Helv. Chim. Acta,* 64, 1552) was added and stirring continued at 0° C. for 2.5 hours. Benzyl ketone of Description 4 (616 mg, 1.8 mmol) as a solution in dichloromethane (6 ml) was added and the reaction mixture allowed to warm to 20° C. overnight. The reaction was quenched by the addition of 1.0M HCl solution (50 ml), extracted with ether (3×30 ml), dried (MgSO$_4$) and concentrated to dryness. The crude oil (200 mg) was purified by flash silica gel chromatography eluting with 2:1 hexane:ether to yield the title compound as a yellow oil (55 mg, 6%). $^1$H NMR (CDCl$_3$) δ 2.28 (1 H, d, J=13.3), 2.22–2.40 (2 H, m), 2.45 (1 H, d, J=13.3), 2.81 (2 H, t, J=11.8), 3.54 (1 H, s), 3.54 (1 H, s), 3.66 (2 H, d, J=12.8), 3.77 (1 H, d, J=9.3), 4.32 (2 H, m), 4.43 (1 H, d, J=9.2), 7.00 (2 H, t, J=8.7), 7.13 (1 H, d, J=7.4), 7.21–7.38 (7 H, m), 7.58 (2 H, br s), 7.68 (1 H, d, J=7.3); m/z (ES$^+$) 488 (M+1, 100%).

EXAMPLES 4A and 4B

(2R,3S,9R)-4-Aza-4-benzyl-1,7-dioxa-3-(4-fluorophenyl)-9-hydroxy-9-(2-methoxy-5-(trifluoromethyl)phenyl)spiro[5,4]decane; and (2R,3S,9S)-4-Aza-4-benzyl-1,7-dioxa-3-(4-fluorophenyl)-9-hydroxy-9-(2-methoxy-5-(trifluoromethyl)phenyl)spiro[5,4]decane 2-Methoxy-5-(trifluoromethyl)iodobenzene (1.51 g, 5.0 mmol) and the benzyl ketone of Description 4 (1.53 g, 4.5 mmol) were reacted according to the method of Example 2 which gave after work up a crude oil (2.2 g). The crude concentrate was purified by flash silica gel chromatography eluting with 6:1 to 4:1 hexane:ethyl acetate to yield the title compound (Example 4A) as a white foam (846 mg, 36%); $^1$H NMR (360 MHz, CDCl$_3$) δ 1.92 (1 H, d, J=13.0), 2.33 (1 H, dt, J=12.0, 3.5), 2.65 (1 H, d, J=13.0), 2.76 (1 H, d, J=13.2), 2.82 (1 H, d, J=11.5), 3.30 (3 H, s), 3.54 (1 H, s), 3.64 (1 H, d, J=13.0), 4.03 (1 H, d, J=8.8), 4.18 (1 H, d, J=8.8), 4.33 (1 H, dt, J=11.8, 2.3), 4.66 (1 H, s), 6.72 (1 H, d, J=8.6), 7.07 (2 H, t, J=8.7), 7.16–7.28 (5 H, m), 7.42 (1 H, dd, J=8.9, 2.2), 7.63 (2 H, br s), 7.98 (1 H, d, J=2.3); m/z (ES$^+$) 518 (M+1, 100%); and the title compound (Example 4B) as an oil (170 mg, 7%); $^1$H NMR (360 MHz, CDCl$_3$) δ 2.22 (1 H, dd, J=14.3, 1.2), 2.33 (1 H, dt, J=11.9, 3.5), 2.73 (1 H, d, J=14.3), 2.81 (1 H, d, J=13.2), 3.52 (1 H, s), 3.57 (1 H, m), 3.70 (1 H, d, J=13.2), 3.84 (3 H, s), 3.85 (1 H, d, J=9.0), 4.22 (1 H, dt, J=11.8, 2.4), 4.35 (1 H, d, J=9.0), 6.88 (1 H, d, J=8.6), 7.12 (2 H, t, J=8.7), 7.18–7.30 (5 H, m), 7.48 (1 H, dd, J=8.4, 1.8), 7.65 (1 H, d, J=2.1), 7.71 (2 H, br s); m/z (ES$^+$) 518 (M+1, 100%).

EXAMPLE 5

(2R,3S,9R)-4-Aza-4-benzyl-1,7-dioxa-3-(4-fluorophenyl)-9-hydroxy-9-(2-(trifluoromethyl)phenyl)spiro[5,4]decane The title compound was prepared according to the method of Example 3 to yield a yellow oil (91 mg, 10%). $^1$H NMR (360 MHz, CDCl$_3$) δ 2.21 (1 H, d, J=13.0), 2.35 (1 H, dt, J=11.9, 3.3), 2.40 (1 H, d, J=13.2), 2.77 (1 H, d, J=13.3), 2.83 (1 H, d, J=11.7), 3.56 (1 H, s), 3.62–3.70 (2 H, m), 3.83 (1 H, d, J=9.3), 4.34 (1 H, dt, J=11.6, 2.1), 4.47 (1 H, d, J=9.3), 4.55 (1 H, s), 7.00 (2 H, t, J=8.7), 7.14–7.35 (9 H, m), 7.57 (2 H, br s); m/z (ES$^+$) 504 (M+1, 100%).

EXAMPLE 6

(+/−)-(2R*,3S*,9R*)-4-Aza-4-benzyl-1,7-dioxa-3-(4-fluorophenyl)-9-hydroxy-9-(2-methylphenyl)spiro[5,4]decane The title compound was prepared according to the method of Example 1 to yield a white foam (355 mg, 47%). Analysis Found: C, 74.64; H, 6.39; N, 3.40. $C_{27}H_{28}FNO_3$ requires C, 74.81; H, 6.51; N, 3.23%. $^1$H NMR (360 MHz, CDCl$_3$) δ 2.14 (3 H, s), 2.27 (1 H, d, J=13.2), 2.33 (1 H, d, J=13.6), 2.35 (1 H, dt, J=11.9, 3.3), 2.80 (1 H, d, J=13.4), 2.83 (1 H, d, J=14.4), 3.57 (1 H, s), 3.67 (1 H, d, J=13.3), 3.86 (1 H, d, J=9.3), 4.28 (1 H, s), 4.33 (1 H, dt, J=11.8, 2.4), 4.43 (1 H, d, J=9.3), 7.00 (2 H, t, J=8.8), 7.04–7.31 (9 H, m), 7.58 (2 H, br s); m/z (ES$^+$) 434 (M+1, 100%).

EXAMPLE 7

(2R,3S,9R)-4-Aza-4-benzyl-1,7-dioxa-9-(2-ethylphenyl)-3-(4-fluorophenyl)-(9-hydroxy-spiro[5,4]decane The title compound was prepared according to the method of Example 2 to yield an oil (180 mg, 28%). $^1$H NMR (360 MHz, CDCl$_3$) δ 1.07 (3 H, t, J=7.5), 2.26–2.48 (4 H, m), 2.77–2.88 (2 H, m), 3.57 (1 H, s), 3.64–3.72 (2 H, m), 3.82 (1 H, d, J=9.3), 4.32–4.38 (2 H, m), 4.41 (1 H, d, J=9.3) 6.98–7.08 (3 H, m), 7.14–7.30 (8 H, m), 7.54–7.64 (2 H, br s); m/z (ES$^+$) 449 (M+1, 100%).

EXAMPLE 8

(2R,3S,9R)-4-Aza-4-benzyl-9-(2-chlorophenyl)-1,7-dioxa-3-(4-fluorophenyl)-(9-hydroxy-spiro[5,4]decane The title compound was prepared according to the method of Example 1 to yield an oil (280 mg, 51%). m/z (ES$^+$) 454 (M+1, 100%).

EXAMPLE 9

(2R,3S,9R)-4-Aza-1,7-dioxa-3-(4-fluorophenyl)-9-hydroxy-9-phenylspiro[5,4]decane The benzylamine of Example 1 (255 mg, 0.61 mmol) as a solution in methanol (15 ml) was hydrogenated at 40 psi of hydrogen with 10% Pd—C catalyst (160 mg) for 2½ hours. The reaction mixture was filtered through a pad of Hyflo™ and concentrated to a crude gum which was purified by flash silica gel chromatography eluting with 5% methanol in dichloromethane to yield the title compound as a glass (76 mg, 38%). $^1$H NMR (360 MHz, CDCl$_3$) δ 1.7–1.9 (~2 H, br s), 2.09 (1 H, d, J=13.5), 2.20 (1 H, dd, J=13.5, 0.9), 3.06 (1 H, dd, J=12.4, 2.4), 3.22 (1 H, dt, J=12.3, 3.6), 3.73 (1 H, dd, J=11.2, 3.0), 3.78 (1 H, d, J=9.3), 4.03 (1 H, s), 4.27 (1 H, d, J=9.3), 4.36 (1 H, dt, J=11.7, 2.7), 7.03 (2 H, t, J=8.07), 7.12 (2 H, m), 7.16–7.26 (3 H, m), 7.47 (2 H, m); m/z (ES$^+$) 330 (M+1, 100%), 312 (M–17, 30).

EXAMPLE 10

(2R,3S,9R)-4-Aza-1,7-dioxa-3-(4-fluorophenyl)-9-hydroxy-9-(2-methoxyphenyl)spiro[5,4]decane The benzylamine of Example 2 was hydrogenated according to the method of Example 9 to yield the title compound as a glass (90 mg, 68%). $^1$H NMR (360 MHz, CDCl$_3$) δ 198 (1 H, d, J=13.1), 2.56 (1 H, d, J=13.1), 3.04 (1 H, dd, J=11.6, 2.1), 3.20 (1 H, dt, J=12.3, 3.7), 3.34 (3 H, s), 3.71 (1 H, dd, J=11.0, 2.6), 4.03 (1 H, s), 4.17 (2 H, s), 4.33 (1 H, dt, J=11.6, 3.1), 6.72 (1 H, dd, J=8.2, 0.9), 6.89 (1 H, dt, J=7.6, 1.1), 7.02 (2 H, t, J=8.7), 7.18 (1 H, dt, J=7.8, 1.8), 7.44–7.55 (3 H, m); m/z (ES$^+$) 360 (M+1, 100%), 342 (M–17, 72), 192 (75).

EXAMPLE 11

(2R,3S,9R)-4-Aza-1,7-dioxa-3-(4-fluorophenyl)-9-hydroxy-9-(2-(trifluoromethyl)phenyl)spiro[5,4]decane The benzylamine of Example 3 was hydrogenated according to the method of Example 9 to yield the title compound as a glass (21 mg, 53%). $^1$H NMR (360 MHz, CDCl$_3$) δ 2.21 (1 H, d, J=13.3), 2.42 (1 H, d, J=13.3), 3.06 (1 H, dd, J=12.4, 2.0), 3.22 (1 H, dt, J=12.3, 3.6), 3.73 (1 H, dd, J=11.2, 2.8), 3.89 (1 H, d, J=9.4), 4.05 (1 H, s), 4.34 (1 H, dt, J=11.7, 2.6), 4.48 (1 H, d, J=9.4), 6.94–7.00 (2 H, m), 7.20 (1 H, d, J=7.3), 7.31–7.47 (4 H, m), 7.68 (1 H, dd, J=7.5, 1.6); m/z (ES$^+$) 398 (M+1, 100%).

EXAMPLE 12

(2R,3S,9R)-4-Aza-1,7-dioxa-3-(4-fluorophenyl)-9-hydroxy-9-(2-methoxy-5-(trifluoromethyl)phenyl)spiro[5,4]decane The benzylamine of Example 4A was hydrogenated according to the method of Example 9 to yield the title compound as an oil (80 mg, 70%). $^1$H NMR (360 MHz, CDCl$_3$) δ 1.7–2.1 (~1 H, br s), 1.91 (1 H, d, J=13.1), 2.59 (1 H, d, J=13.0), 3.06 (1 H, dd, J=12.4, 2.0), 3.22 (1 H, dt, J=12.3, 3.6), 3.32 (3 H, s), 3.73 (1 H, dd, J=11.1, 2.7), 4.04 (1 H, s), 4.07 (1 H, d, J=8.9), 4.34 (1 H, dt, J=11.7, 2.9), 6.75 (1 H, d, J=8.6), 7.04 (2 H, t, J=8.6), 7.43–7.52 (3 H, m), 7.92 (1 H, d, J=2.3); m/z (ES$^+$) 428 (M+1, 100%).

EXAMPLE 13

(2R,3S,9S)-4-Aza-1,7-dioxa-3-(4-fluorophenyl)-9-hydroxy-9-(2-methoxy-5-(trifluoromethyl)phenyl)spiro[5,4]decane The benzylamine of Example 4B was hydrogenated according to the method of Example 9 to yield the title compound as an oil (79 mg, 68%). $^1$H NMR (360 MHz, CDCl$_3$) δ 2.14 (1 H, d, J=14.3), 2.16 (~1 H, br s), 2.64 (1 H, d, J=14.4), 3.02 (1 H, dd, J=12.3, 2.2), 3.18 (1 H, dt, J=12.2, 3.6), 3.62 (1 H, dd, J=11.4, 2.8), 3.86 (3 H, s), 3.91 (1 H, dd, J=9.2, 1.3), 3.99 (1 H, s), 4.22 (1 H, dt, J=11.8, 2.6), 4.36 (1 H, d, J=9.0), 6.90 (1 H, d, J=8.6), 7.07 (2 H, t, J=8.7), 7.49 (1 H, dd, J=8.2, 1.8), 7.54–7.63 (3 H, m); m/z (ES$^+$) 428 (M+1, 100%).

EXAMPLE 14

(2R,3S,9R)-4-Aza-1,7-dioxa-3-(4-fluorophenyl)-9-hydroxy-9-(2-(trifluoromethoxy)phenyl)spiro[5,4]decane The benzylamine of Example 5 was hydrogenated according to the method of Example 9 to yield the title compound as an oil (46 mg, 68%). $^1$H NMR (360 MHz, CDCl$_3$) δ 1.7–2.1 (1 H, br s), 2.18 (1 H, d, J=13.1), 2.33 (1 H, d, J=13.2), 3.06 (1 H, dd, J=12.4, 2.2), 3.22 (1 H, dt, J=12.3, 3.6), 3.74 (1 H, dd, J=11.3, 2.9), 3.97 (1 H, d, J=9.4), 4.06 (1 H, s), 4.35 (1 H, dt, J=11.7, 2.4), 4.48 (1 H, d, J=9.5), 6.97 (2 H, m), 7.24–7.30 (1 H, m), 7.39–7.46 (3 H, m); m/z (ES$^+$) 414 (M+1, 100%).

EXAMPLE 15

(+/–)-(2R*,3S*,9R*)-4-Aza-1,7-dioxa-3-(4-fluorophenyl)-9-hydroxy-9-(2-methylphenyl)spiro[5,4]decane The benzylamine of Example 6 was hydrogenated according to the method of Example 9 to yield the title compound as glass (105 mg, 78%). $^1$H NMR (360 MHz, CDCl$_3$) δ 2.19 (1 H, d, J=12.9), 2.21 (3 H, s), 2.31 (1 H, d, J=13.2), 2.9–3.3 (~2 H, br s), 3.05 (1 H, dd, J=11.7, 2.0), 3.21 (1 H, dt, J=12.3, 3.6), 3.72 (1 H, dd, J=10.5, 2.7), 3.95 (1 H, d, J=9.3), 4.06 (1 H, s), 4.34 (1 H, dt, J=11.7, 3.0), 4.49 (1 H, d, J=9.2), 6.94–7.18 (6 H, m), 7.42–7.47 (2 H, m); m/z (ES$^+$) 344 (M+1, 100%).

EXAMPLE 16

(2R,3S,9R)-4-Aza-4-(2,3-dihydro-3-oxo-1,2,4-triazol-5-yl)methyl-1,7-dioxa-3-(4-fluorophenyl)-9-hydroxy-9-(2-methoxyphenyl)spiro[5,4]decane The morpholine of Example 10 (81 mg, 0.23 mmol) was heated with N-methylcarboxy-2-chloroacetamidrazone (see European Patent Specification No. 0 577 394-A) (45 mg, 0.271 mmol) and potassium carbonate (125 mg, 0.904 mmol) in DMF (5 ml) at 60° C. for 1 hour. The cooled solution was diluted with water (25 ml), extracted with ethyl acetate (3×15 ml), dried (MgSO$_4$) and concentrated to dryness. The crude gum (110 mg) was purified by flash silica gel chromatography eluting with 6–8% methanol in dichloromethane to yield the intermediate imidiazone, which was redissolved in xylene (2 ml) and heated at reflux for 2 hours. The crude concentrate was purified by flash silica gel chromatography eluting with 6% methanol in dichloromethane to yield the title compound as a glass (42 mg, 41%). $^1$H NMR (360 MHz, CDCl$_3$) δ 2.05 (1 H, d, J=13.1), 2.57 (1 H, d, J=13.2), 2.61 (1 H, m), 2.89 (1 H, br d, J=11.2 ), 2.95 (1 H, d, J=14.5), 3.35 (3 H, s), 3.45 (1 H, d, J=14.5), 3.62 (1 H, s), 3.75 (1 H, br d, J=8.9), 4.14 (1 H, d, J=9.0), 4.18 (1 H, d, J=9.0), 4.36 (1 H, dt, J=11.7, 2.1), 4.47 (1 H, s), 6.71 (1 H, d, J=8.2), 6.89 (1 H, t, J=7.5), 7.05 (2 H, t, J=8.6), 7.19 (1 H, t, J=7.5), 7.50 (1 H, dd, J=7.8, 1.6), 7.56 (2 H, vbr s), 9.90 (1 H, br s), 10.45 (1 H, br s); m/z (ES$^+$) 457 (M+1, 32%), 439 (M−17, 15), 382 (100).

EXAMPLE 17

(2R,3S,9R)-4-Aza-4-(2,3-dihydro-3-oxo-1,2,4-triazol-5-yl)methyl-1,7-dioxa-3-(4-fluorophenyl)-9-hydroxy-9-(2-(trifluoromethyl)phenyl)-spiro[5,4]decane The title compound was prepared from the morpholine of Example 11 according to the method of Example 16 to yield a glass (60 mg, 48%). $^1$H NMR (360 MHz, CDCl$_3$) δ 2.2–2.5 (1 H, br s), 2.23 (1 H, d, J=13.5), 2.47 (1 H, d, J=13.4), 2.61 (1 H, dt, J=11.9, 3.3), 2.90 (1 H, d, J=11.3), 3.00 (1 H, d, J=14.4), 3.47 (1 H, d, J=14.5), 3.61 (1 H, s), 3.75 (1 H, d, J=8.9), 3.81 (1 H, d, J=9.3), 4.26 (1 H, s), 4.35 (1 H, dt, J=11.7, 2.0), 4.45 (1 H, d, J=9.3), 6.99 (2 H, t, J=8.6), 7.11 (1 H, d, J=8.6), 7.31–7.37 (2 H, m), 7.52 (2 H, br s), 7.67 (1 H, d, J=9.3), 10.41 (1 H, s), 10.95 (1 H, br s); m/z (ES$^+$) 495 (M+1, 100%).

EXAMPLE 18

(2R,3S,9R)-4-Aza-4-(4-(N,N-dimethylamino)-but-2-ynyl)-1,7-dioxa-3-(4-fluorophenyl)-9-hydroxy-9-(2-methoxy-5-(trifluoromethyl)phenyl)-spiro[5,4]decane The chloride of Description 5 (60 mg, 0.12 mmol) dissolved in dioxan (3 ml) was added to condensed dimethylamine (3 ml) in a sealed tube and heated at 90° C. for 7 hours. The crude concentrate was purified by flash silica gel chromatography eluting with 5% methanol in dichloromethane to yield the title compound as an oil (42 mg, 69%). $^1$H NMR (360 MHz, CDCl$_3$) δ 1.92 (1 H, d, J=13.0), 2.31 (6 H, s), 2.32 (2 H, s), 2.56 (1 H, d, J=13.1), 2.83 (1 H, br d, J=11.6), 3.03 (1 H, dt, J=12.0, 3.7), 3.29 (2 H, s), 3.32 (3 H, s), 3.75 (1 H, s), 3.79 (1 H, dd, J=11.3, 3.7), 4.06 (1 H, d, J=8.9), 4.19 (1 H, d, J=8.9), 4.46 (1 H, dt, J=11.6, 2.3), 4.61 (~1 H, br s), 6.75 (1 H, d, J=8.6), 7.05 (2 H, t, J=8.5), 7.44 (1 H, dd, J=9.0, 2.6), 7.53 (2 H, br s), 7.92 (1 H, d, J=2.2); m/z (ES$^+$) 523 (M+1, 100%).

EXAMPLE 19

(2R,3S,9R)-4-Aza-4-(5-(N,N-dimethylaminomethyl)-1,2,3-triazol-4-yl)methyl-1,7-dioxa-3-(4-fluorophenyl)-9-hydroxy-9-(2-methoxy-5-(trifluoromethyl)phenyl)spiro[5,4]decane The azide of Description 6 (230 mg, 0.44 mmol) dissolved in dioxan (6 ml) was added to condensed dimethylamine (6 ml) in a sealed tube and heated at 90° C. for 7 hours. The crude concentrate was purified by flash silica gel chromatography eluting with 10% methanol in dichloromethane to yield the title compound as a foam (155 mg, 62%). $^1$H NMR (360 MHz, CDCl$_3$) δ 1.94 (1 H, d, J=13.0), 2.23 (6 H, s), 2.55 (1 H, m), 2.58 (1 H, d, J=13.1), 2.87 (1 H, d, J=11.5), 3.20 (1 H, d, J=13.8), 3.34 (3 H, s), 3.51 (2 H, s), 3.61 (2 H, t, J=6.9), 3.71 (1 H, dd, J=11.3, 2.1), 4.05 (1 H, d, J=8.9), 4.18 (1 H, d, J=8.9), 4.32 (1 H, dt, J=11.7, 2.0), 6.75 (1 H, d, J=8.6), 7.09 (2 H, t, J=8.6), 7.45 (1 H, dd, J=8.3, 2.1), 7.62 (2 H, br s), 7.91 (1 H, d, J=2.2); m/z (ES$^+$) 566 (M+1, 82%), 165 (100).

EXAMPLES 20A and 20B

(2R,3S,9R)-4-Aza-1,7-dioxa-3-(4-fluorophenyl)-9-hydroxy-4-(1(S)-phenylethyl)-9-(2-(trifluoromethyl)phenyl)spiro[5,4]decane; and (2R,3S,9R)-4-Aza-1,7-dioxa-3-(4-fluorophenyl)-9-hydroxy-4-(1(R)-phenylethyl)-9-(2-(trifluoromethyl)phenyl)spiro[5,4]decane (1-Bromoethyl)benzene (103 μl, 0.76 mmol) and potassium carbonate (208 mg, 1.5 mmol) were added to the morpholine of Example 11 (150 mg, 0.38 mmol) as a solution in DMF (7 ml) and stirred for 18 hours at 20° C., then 4 hours at 75° C. The cooled reaction mixture was diluted with water (50 ml), extracted with ether (3×25 ml), dried (MgSO$_4$) and concentrated to a yellow oil (194 mg). The crude isomers were separated by medium pressure chromatography eluting with 2:1 hexane:ether to yield the less polar title compound (Example 20A) as a white solid (39 mg, 21%); $^1$H NMR (360 MHz, CDCl$_3$) δ 1.17 (3 H, d, J=6.8), 2.24 (1 H, d, J=13.3), 2.41 (1 H, d, J=11.6), 2.45 (1 H, d, J=13.3), 2.65 (1 H, dt, J=11.8, 3.3), 3.62 (1 H, m), 3.75 (1 H, q, J=6.8), 3.77 (1 H, d, J=9.2), 3.93 (1 H, s), 4.24 (1 H, dt, J=11.4, 1.9), 4.36 (1 H, s), 4.44 (1 H, d, J=9.2), 6.99 (2 H, t, J=8.8), 7.15 (1 H, d, J=7.3), 7.18–7.40 (4 H, m), 7.43 (2 H, d, J=8.0), 7.64 (2 H, br s), 7.68 (1 H, dd, J=7.6, 1.6); m/z (ES$^+$) 502 (M+1, 100%); and the more polar title compound (Example 20B) as a glass (68 mg, 36%); $^1$H NMR (360 MHz, CDCl$_3$) δ 1.39 (3 H, d, J=7.1), 2.20 (1 H, d, J=13.5), 2.30 (1 H, d, J=13.4), 2.30 (1 H, m), 3.00 (1 H, d, J=11.5), 3.48 (1 H, s), 3.66 (1 H, d, J=9.3), 3.71 (1 H, dd, J=11.0, 1.4), 3.82 (1 H, q, J=7.1), 4.21 (1 H, s), 4.36 (2 H, m), 6.95 (2 H, dd, J=8.0, 1.6), 7.04 (2 H, t, J=8.7), 7.05 (1 H, m), 7.23–7.36 (5 H, m), 7.51 (2 H, br s), 7.65 (1 H, dd, J=7.3, 2.0); m/z (ES$^+$) 502 (M+1, 100%).

EXAMPLE 21

(2R,3S,9R)-4-Aza-1,7-dioxa-3-(4-fluorophenyl)-9-hydroxy-4-((2-(trifluoromethyl)phenyl)methyl)-9-(2-(trifluoromethyl)phenyl)-spiro[5,4]decane The morpholine of Example 11 (100 mg, 0.25 mmol), 2-(trifluoromethyl)benzyl bromide (120 mg, 0.50 mmol) and potassium carbonate (138 mg, 1.00 mmol) were stirred in DMF (5 ml) for 4 hours. The reaction mixture was diluted with water (50 ml), extracted with ether, (3×25 ml), dried (MgSO$_4$) and concentrated to a crude oil (244 mg) which was purified by flash silica gel chromatography eluting with 4:1 hexane:ethyl acetate to yield the title compound as a glass (99 mg, 71%). $^1$H NMR (360 MHz, CDCl$_3$) δ 2.29 (1 H, d, J=13.3), 2.44 (1 H, dt, J=12.0, 3.2), 2.47 (1 H, d, J=13.3), 2.75 (1 H, d, J=11.8), 3.23 (1 H, dd, J=14.8, 1.8), 3.58 (1 H, d, J=14.8), 3.66 (1 H, s), 3.67 (1 H, m), 3.79 (1 H, d, J=9.3), 4.32 (1 H, s), 4.36 (1 H, dt, J=11.7, 2.4), 4.46 (1 H, d, J=9.3), 6.95 (2 H, t, J=8.8), 7.15 (1 H, d, J=7.3), 7.24–7.39 (3 H, m), 7.51–7.65 (~4 H, m), 7.68 (1 H, dd, J=7.5, 1.6), 7.96 (1 H, dd, J=7.7); m/z (ES$^+$) 556 (M+1, 100%).

EXAMPLE 22

(+/−)-(2R*,3S*,9R*)-4-Aza-4-benzyl-1,7-dioxa-3-(4-fluorophenyl)-9-methoxy-9-phenyl-spiro[5,4]decane Sodium hydride (80 mg, 60% dispersion in oil, 2.0 mmol), was added to a racemic mixture of the alcohol of Example 1 (250 mg, 0.60 mmol) dissolved in DMF (5 ml). After stirring for 30 minutes, methyl iodide (370 μl, 5.96 mmol) was added and the reaction stirred for between 2 and 24 hours. The reaction mixture was quenched by the addition of water (50 ml, care!) extracted with ether (3×25 ml), dried (MgSO$_4$) and concentrated to a yellow solid (254 mg) which was purified by flash silica gel chromatography eluting with 5:1 hexane:ethyl acetate to yield the title compound as a glass (197 mg, 76%). Analysis Found: C, 75.10; H, 6.51; N, 3.38. C$_{27}$H$_{28}$FNO$_3$ requires C, 74.81; H, 6.51; N, 3.23%). $^1$H NMR (360 MHz, CDCl$_3$) δ 2.22 (1 H, d, J=14.2), 2.33 (1 H, dt, J=11.9, 3.4), 2.45 (1 H, d, J=14.2), 2.79 (2 H, m), 3.09 (3 H, s), 3.45 (1 H, s), 3.64–3.70 (3 H, m), 4.24 (1 H, dt, J=11.7, 2.2), 4.28 (1 H, d, J=9.3), 6.77–6.83 (2 H, m), 6.97 (2 H, t, J=8.7), 7.11–7.26 (8 H, m), 7.57 (~2 H, br s); m/z (ES$^+$) 434 (M+1, 100%), 402 (M−31, 42).

EXAMPLE 23

(2R,3S,9R)-4-Aza-4-benzyl-1,7-dioxa-3-(4-fluorophenyl)-9-methoxy-9-(2-methoxyphenyl)spiro[5,4]decane The alcohol of Example 2 was reacted according to the method of Example 22 to yield the title compound as a pale yellow foam (466 mg, 71%). $^1$H NMR (360 MHz, CDCl$_3$) δ 2.25 (1 H, d, J=13.9), 2.31 (1 H, dt, J=11.9, 3.4), 2.58 (1 H, dd, J=13.8, 1.0), 2.75 (1 H, d, J=13.1), 2.78 (1 H, br d), J=11.3), 2.97 (3 H, s), 3.45 (1 H, s), 3.60 (1 H, d, J=13.3), 3.62–3.69 (2 H, m), 3.66 (3 H, s), 4.28 (1 H, dt, J=11.8, 2.2), 4.52 (1 H, dd, J=9.8, 0.8), 6.77–6.83 (2 H, m), 6.88–6.97 (3 H, m), 7.17–7.27 (6 H, m), 7.56 (~2 H, br s); m/z (ES$^+$) 464 (M+1, 100%).

EXAMPLE 24

(2R,3S,9R)-4-Aza-4-benzyl-1,7-dioxa-3-(4-fluorophenyl)-9-methoxy-9-(2-(trifluoromethyl)phenyl)spiro[5,4]decane The alcohol of Example 3 was reacted according to the method of Example 22 to yield the title compound as a solid after recrystallisation from 60/80 petrol (910 mg, 82%). Mp. 155–157° C. (petrol). $^1$H NMR (360 MHz, CDCl$_3$) δ 2.29 (1 H, d, J=14.7), 2.27–2.41 (1 H, m), 2.56 (1 H, d, J=14.7), 2.72–2.83 (2 H, m), 2.96 (3 H, s), 3.35 (1 H, s), 3.59–3.70 (2 H, m), 4.18 (1 H, br t, J=11.8), 4.27 (2 H, s), 6.63 (1 H, d, J=7.9), 6.75 (1 H, br s), 7.08 (1 H, t, J=7.4), 7.16–7.46 (8 H, m), 7.59 (1 H, d, J=7.9).

EXAMPLE 25

(2R,3S,9R)-4-Aza-4-benzyl-1,7-dioxa-3-(4-fluorophenyl)-9-methoxy-9-(2-methoxy-5-(trifluoromethyl)phenyl)spiro[5,4]decane The alcohol of Example 4A was reacted according to the method of Example 22 to yield the title compound as a foam (430 mg, 67%). $^1$H NMR (360 MHz, CDCl$_3$) δ 2.32 (1 H, dt, J=11.9, 3.5), 2.35 (1 H, d, J=14.0), 2.53 (1 H, d, J=14.0), 2.75 (1 H, d, J=13.1), 2.79 (1 H, d, J=11.0), 2.97 (3 H, s), 3.43 (1 H, s), 3.59 (1 H, d, J=13.3), 3.64 (1 H, m), 3.69 (3 H, s), 3.82 (1 H, d, J=8.6), 6.88 (2 H, t, J=8.7), 7.17–7.29 (6 H, m), 7.46 (1 H, dd, J=8.4, 1.6), 7.51 (~2 H, br s); m/z (ES$^+$) 532 (M+1, 100%).

EXAMPLE 26

(+/−)-(2R*,3S*,9R*)-4-Aza-4-benzyl-1,7-dioxa-3-(4-fluorophenyl)-9-methoxy-9-(2-methylphenyl)spiro[5,4]decane The alcohol of Example 6 was reacted according to the method of Example 22 to yield the title compound as an oil (175 mg, 39%). $^1$H NMR (360 MHz, CDCl$_3$) δ 2.28–2.36 (2H, m), 2.31 (3H, s), 2.54 (1H, d, J=13.8), 2.76 (1H, d, J=13.1), 2.79 (1H, d, J=11.6), 2.87 (3H, s), 3.42 (1H, s), 3.63 (1H, d, J=13.2), 3.65 (1H, m), 3.89 (1H, d, J=9.3), 4.26 (1H, dt, J=11.8, 2.5), 4.42 (1H, d, J=9.3), 6.65 (1H, d, J=7.7), 6.84 (2H, t, J=8.9), 6.90 (1H, m), 7.05 (2H, m), 7.15–7.27 (5H, m), 7.49 (~2H, br s); m/z (ES$^+$) 448 (M+1, 100%).

EXAMPLE 27

(2R,3S,9R)-4-Aza-4-benzyl-1,7-dioxa-9-(2-ethylphenyl)-3-(4-fluorophenyl)-9-methoxy-spiro[5.4]decane The alcohol of Example 7 was reacted according to the method of Example 22 to yield the title compound as a white solid (135 mg, 77%). $^1$H NMR (360 MHz, CDCl$_3$) δ 1.14 (1H, t, J=7.5), 2.28–2.37 (2H, m), 2.54 (1H, d, J=13.8), 2.67–2.84 (4H, m), 2.89 (3H, s), 3.42 (1H, s), 3.60–3.69 (2H, m), 3.85 (1H, d, J=9.4), 4.25 (1H, td, J=10.6, 2.2), 4.41 (1H, d, J=9.4), 6.67 (1H, d, J=7.9), 6.80–6.93 (3H, m), 7.11–7.28 (7H, m), 7.47 (2H. br s); m/z (ES$^+$) 462 (M+1, 100%).

EXAMPLE 28

(2R,3S,9R)-4-Aza-4-benzyl-9-(2-chlorophenyl)-1,7-dioxa-3-(4-fluorophenyl)-9-methoxy-spiro[5,4]decane The alcohol of Example 8 was reacted according to the method of Example 22 to yield the title compound as an oil (150 mg, 51%). $^1$H NMR (360 MHz, CDCl$_3$) δ 2.31 (1H, td, J=11.9, 3.3), 2.45 (1H, d, J=14.1), 2.68 (1H, d, J=14.1), 2.73–2.84 (2H, m), 2.92 (3H, s), 3.41 (1H, s), 3.60–3.69 (2H, m), 4.05 (1H, d, J=9.7), 4.23 (1H, td, J=11.7, 2.2), 4.45 (1H, d, J=9.7), 6.78–6.86 (2H, m), 6.98 (1H, td, J=7.5, 1.3), 7.10 (1H, td, J=7.7, 1.6), 7.16–7.28 (7H, m), 7.41–7.54 (2H, m); m/z (ES$^+$) 468 (M+1, 100%).

EXAMPLE 29

(+/−)-(2R*,3S*,9R*)-4-Aza-1,7-dioxa-3-(4-fluorophenyl)-9-methoxy-9-phenyl-spiro[5,4]decane The (+/−)-benzylamine of Example 22 was hydrogenated according to the method of Example 9 to yield the title compound as an oil (138 mg, 100%). $^1$H NMR (360 MHz, CDCl$_3$) δ 2.14 (1H, d, J=14.2), 2.40 (1H, d, J=14.2), 3.03 (1H, dd, J=12.3, 2.2), 3.08 (3H, s), 3.20 (1H, dt, J=12.2, 3.6), 3.72 (1H, br d, J=12.1), 3.75 (1H, d, J=9.3), 3.95 (1H, s), 4.26 (1H, dt, J=12.0, 2.7), 4.31 (1H, d, J=9.7), 6.81–6.86 (2H, m), 6.90–6.96 (2H, m), 7.11–7.15 (3H, m), 7.39–7.45 (2H, m); m/z (ES$^+$) 344 (M+1, 60%), 312 (M−31, 100).

EXAMPLE 30

2R,3S,9R)-4-Aza-1,7-dioxa-3-(4-fluorophenyl)-9-methoxy-9-(2-methoxyphenyl)spiro[5.4]decane The benzylamine of Example 23 was hydrogenated according to the method of Example 9 to yield the title compound as a yellow oil (265 mg, 84%). $^1$H NMR (360 MHz, CDCl$_3$) δ 2.18 (1H, d, J=13.9), 2.54 (1H, d, J=13.9), 2.99 (3H, s), 3.00 (1H, m), 3.16 (1H, dt, J=12.2, 3.6), 3.63 (3H, s), 3.70 (1H, dd, J=11.4, 2.9), 3.82 (1H, d, J=9.8), 3.95 (1H, s), 4.30 (1H, dt, J=11.8, 2.7), 4.55 (1H, d, J=9.8), 6.77–6.93 (4H, m), 6.98 (1H, dd, J=7.6, 1.6), 7.19 (1H, dt, J=7.8, 1.7), 7.39–7.45 (2H, m); m/z (ES$^+$) 374 (M+1, 100%), 342 (M−31, 93).

EXAMPLE 31

(2R,3S,9R)-4-Aza-1,7-dioxa-3-(4-fluorophenyl)-9-methoxy-9-(2-(trifluoromethyl)phenyl)spiro[5.4]decane The benzylamine of Example 24 was hydrogenated according to the method of Example 9 to yield the title compound as a white solid (603 mg, 90%). $^1$H NMR (360 MHz, CDCl$_3$) δ 2.01 (1H, br s, NH), 2.26 (1H, d, J=14.6), 2.52 (1H, d, J=14.6), 2.96 (3H, s), 3.03 (1H, dt, J=14.0, 2.0), 3.17 (1H, td, J=12.1, 4.0), 3.70 (1H, dd, J=11.4, 3.0), 3.46 (1H, s), 4.21 (1H, td, J=11.9, 2.9), 4.30 (2H, s), 6.65–6.78 (3H, m), 7.06 (1H, t, J=7.6), 7.18–7.31 (3H, m), 7.58 (1H, d, J=7.9); m/z (ES$^+$) 412 (M+1, 100%).

EXAMPLE 32

(2R,3S,9R)-4-Aza-1,7-dioxa-3-(4-fluorophenyl)-9-methoxy-9-(2-methoxy-5-(trifluoromethyl)phenyl)spiro[5.4]decane The benzylamine of Example 25 was hydrogenated according to the method of Example 9 to yield the title compound as an oil (272 mg, 88%). $^1$H NMR (360 MHz, CDCl$_3$) δ 2.26 (1H, d, J=13.9), 2.2–2.5 (~2H, br s), 2.49 (1H, d, J=13.7), 3.00 (3H, s), 3.03 (1H, m), 3.16 (1H, dt, J=12.2, 3.7), 3.64 (3H, s), 3.71 (1H, dd, J=11.5, 2.8), 3.93 (1H, d, J=9.8), 3.96 (1H, s), 4.31 (1H, dt, J=11.9, 2.9), 4.44 (1H, d, J=9.7), 6.81 (1H, d, J=8.6), 6.88 (2H, t, J=8.7), 7.25 (1H, d, J=2.1), 7.39–7.47 (3H, m); m/z (ES$^+$) 442 (M+1, 100%).

EXAMPLE 33

(2R,3S,9R)-4-Aza-1,7-dioxa-3-(4-fluorophenyl)-9-methoxy-9-(2-methylphenyl)spiro[5.4]decane The benzylamine of Example 26 was hydrogenated according to the method of Example 9 to yield the title compound as a glass (35 mg, 47%). $^1$H NMR (360 MHz, CDCl$_3$) δ 2.14 (1H, d, J=13.9), 2.16 (1H, m), 2.28 (3H, s), 2.56 (1H, d, J=13.9), 2.86 (3H, s), 3.05–3.20 (2H, m), 3.76 (1H, dd, J=12.2, 2.9), 4.05 (1H, d, J=9.5), 4.13 (1H, m), 4.46 (1H, m), 4.49 (1H, d, J=9.5), 6.64 (1H, d, J=7.6), 6.84 (2H, t, J=8.5), 6.88 (1H, m), 7.03–7.10 (2H, m), 7.49 (2H, dd, J=8.5, 5.3); m/z (ES$^+$) 358 (M+1, 100%).

EXAMPLE 34

(2R,3S,9R)-4-Aza-1,7-dioxa-9-(2-ethylphenyl)-3-(4-fluorophenyl)-9-methoxy-spiro[5.4]decane The benzylamine of Example 27 was hydrogenated according to the method of Example 9 to yield the title compound as an oil (85 mg, 81%). $^1$H NMR (250 MHz, CDCl$_3$) δ 1.14 (3H, t, J=10.7), 2.07 (1H, br s), 2.22 (1H, d, J=19.9), 2.49 (1H, d, J=19.9), 2.68 (2H, q, J=10.8), 2.90 (3H, s), 3.02 (1H, dd, J=17.5, 3.4), 3.18 (1H, td, J=17.3, 5.0), 3.72 (1H, td, J=16.5, 4.2), 3.92–3.99 (2H, m), 4.27 (1H, td, J=16.9, 4.3), 4.47 (1H, d, J=13.5), 6.71 (1H, d, J=11.1), 6.76–6.96 (3H, m), 7.11–7.19 (2H, m), 7.30–7.42 (2H, m).

EXAMPLE 35

(2R,3S,9R)-4-Aza-4-(5-(N,N-dimethylaminomethyl)-1,2,3-triazol-4-yl)methyl-1,7-dioxa-3-(4-fluorophenyl)-9-methoxy-9-(2-methoxy-5-(trifluoromethyl)phenyl)spiro[5.4]decane The title compound was prepared from the azide of Description 8 according to the method of Example 19 to yield a foam (86 mg, 76%). $^1$H NMR (360 MHz, CDCl$_3$) δ 2.24 (1H, d, J=14.0), 2.50 (6H, s), 2.55 (1H, d, J=14.0), 2.76 (1H, br d, J=11.2), 2.97 (3H, s), 3.24 (1H, d, J=13.9), 3.50 (1H, s), 3.55 (1H, d, J=14.0), 3.68 (1H, m), 3.69 (3H, s), 3.86 (3H, m), 4.19 (1H, dt, J=11.8, 2.1), 4.47 (1H, d, J=9.8), 6.84 (1H, d, J=8.6), 6.95 (2H, t, J=8.5), 7.21 (1H, d, J=1.9), 7.47 (1H, dd, J=8.7, 1.9), 7.5 (~2H, br s), 7.8–8.4 (~1H, br s); m/z (ES$^+$) 580 (M+1, 100%).

EXAMPLE 36

(2R,3S,9R)-4-Aza-4-(5-(N,N-dimethylaminomethyl)-1,2,3-tetrazol-4-yl)methyl-1,7-dioxa-3-(4-fluorophenyl)-9-methoxy-9-(2-(trifluoromethyl)phenyl)spiro[5.4]decane The title compound was prepared from the azide of Description 10 according to the method of Example 19 to yield a yellow foam (124 mg, 69%). $^1$H NMR (360 MHz, CDCl$_3$) δ 2.19–2.27 (7H, m), 2.50–2.61 (2H, m), 2.82 (1H, br d, J=11.6), 2.96 (3H, s), 3.20 (1H, d, J=14.0), 3.41 (1H, s), 3.48 (2H, s), 3.61 (1H, d, J=14.0), 3.64 (1H, br d, J=1.0), 4.16 (1H, dt, J=9.4, 2.3), 4.25 (1H, d, J=9.8), 4.29 (1H, d, J=4.3), 6.64 (1H, d, J=7.9), 6.79 (1H, br s), 7.10 (1H, t, J=7.6), 7.23 (1H, t, J=7.7), 7.60 (1H, d, J=7.9); m/z (ES$^+$) 550 (M+1, 100%).

EXAMPLES 37A and 37B (2R,3S,9R)-4-Aza-1,7-dioxa-3-(4-fluorophenyl)-9-methoxy-4-(1-(S)-phenylethyl)-9-(2-methoxy-5-(trifluoromethyl)phenyl)spiro[5.4]decane; and (2R,3S,9R)-4-Aza-1,7-dioxa-3-(4-fluorophenyl)-9-methoxy-4-(1-(R)-phenylethyl)-9-(2-methoxy-5-(trifluoromethyl)phenyl)spiro[5.4]decane The morpholine of Example 32 was reacted according to the method of Example 20 to yield the less polar title compound (Example 37A) as an oil (39 mg, 25%), $^1$H NMR (360 MHz, CDCl$_3$) δ 1.14 (3H, d, J=6.9), 2.32 (1H, d, J=14.0), 2.36 (1H, d, J=11.7), 2.53 (1H, d, J=14.2), 2.62 (1H, dt, J=11.7, 3.3), 2.97 (3H, s), 3.60 (1H, dd, J=11.1, 1.7), 3.67 (1H, q, J=6.8), 3.69 (3H, s), 3.83 (2H, m), 4.17 (1H, dt, J=11.4, 2.1), 4.3 (1H, d, J=9.7), 6.81 (1H, d, J=8.6), 6.88 (2H, t, J=8.7), 7.17–7.42 (7H, m), 7.46 (1H, dd, J=8.7, 1.6), 7.58 (~2H, br s); m/z (ES$^+$) 546 (M+1, 100%); and the more polar title compound (Example 37B) as an oil (47 mg, 30%), $^1$H NMR (360 MHz, CDCl$_3$) δ 1.35 (3H, d, J=7.1), 2.19–2.34 (~3H, m), 2.42 (1H, d, 14.0), 2.90 (3H, s), 2.96 (1H, d, J=11.4), 3.37 (1H, s), 3.69 (3H, s), 3.70–3.77 (3H, m), 4.28 (1H, dt, J=11.4, 2.4), 4.35 (1H, d, J=10.0), 6.80 (1H, d, J=8.6), 6.88–6.99 (4H, m), 7.16 (1H, d, J=1.9), 7.20–7.29 (3H, m), 7.41–7.49 (~4H, m); m/z (ES$^{30}$ ) 546 (M+1, 100%).

EXAMPLE 38

(2R,3S,9R)-4-Aza-1,7-dioxa-3-(4-fluorophenyl)-9-methoxy-9-(2-methoxy-5-(trifluoromethyl)phenyl)-4-((2-(trifluoromethyl)phenyl)methyl)spiro[5.4]decane The title compound was prepared from the morpholine of Example 32 according to the method of Example 21 to yield a glass (67 mg, 73%). $^1$H NMR (360 MHz, CDCl$_3$) δ 2.32–2.43 (2H, m), 2.57 (1H, d, J=14.1), 2.71 (1H, br d, J=11.6), 2.99 (3H, s), 3.18 (1H, dd, J=14.7, 1.7) 3.50 (1H, d, J=14.9), 3.54 (1H, s), 3.65 (1H, dt, J=11.5, 1.6), 3.69 (3H, s), 3.83 (1H, d, J=9.8), 4.29 (1H, dt, J=11.8, 2.2), 4.45 (1H, d, J=9.7), 6.81–6.91 (3H, m), 7.24–7.30 (2H, m), 7.45–7.55 (~5H, m), 7.95 (1H, d, J=7.7); m/z (ES$^+$) 600 (M+1, 100%).

EXAMPLE 39

(2R,3S,9R)-4-Aza-1,7-dioxa-3-(4-fluorophenyl)-9-methoxy-9-(2-methoxy-5-(trifluoromethyl)phenyl)-4-((3-(trifluoromethyl)phenyl)methyl)spiro[5.4]decane The title compound was prepared from the morpholine of Example 32 according to the method of Example 21 to yield a glass (54 mg, 59%). $^1$H NMR (360 MHz, CDCl$_3$) δ 2.26 (1H, d, J=14.0), 2.28 (1H, m), 2.47 (1H, d, J=14.0), 2.67 (1H, br d, J=11.4), 2.77 (1H, d, J=13.5), 2.90 (3H, s), 3.38 (1H, s), 3.54 (1H, d, J=13.6), 3.59 (1H, m), 3.62 (3H, s), 3.76 (1H, d, J=9.8), 4.20 (1H, dt, J=11.8, 2.2), 4.35 (1H, d, J=9.8), 6.75 (1H, d, J=8.6), 6.81 (2H, t, J=8.7), 7.15 (1H, d, J=2.1), 7.28–7.41 (5H, m), 7.44 (~2H, br s): m/z (ES$^+$) 600 (M+1, 100%).

EXAMPLE 40

(2R,3S,9R)-4-Aza-1,7-dioxa-3-(4-fluorophenyl)-9-methoxy-9-(2-methoxy-5-(trifluoromethyl)phenyl)-4-((4-(trifluoromethyl)phenyl)methyl)spiro[5.4]decane The title compound was prepared from the morpholine of Example 32 according to the method of Example 21 to yield a glass (63 mg, 69%). $^1$H NMR (360 MHz, CDCl$_3$) δ 2.34 (1H, d, J=14.0), 2.36 (1H, dt, J=11.7, 3.4), 2.55 (1H, d, J=14.0), 2.74 (1H, br d, J=11.5), 2.84 (1H, d, J=13.7), 2.98 (3H, s), 3.46 (1H, s), 3.62 (1H, d, J=14.3), 3.68 (1H, m), 3.70 (3H, s), 3.83 (1H, d, J=9.8), 4.27 (1H, dt, J=12.0, 2.6), 4.44 (1H, d, J=9.8), 6.83 (1H, d, J=8.6), 6.88 (2H, t, J=8.7), 7.23 (1H, d, J=2.1), 7.36 (2H, d, J=8.0), 7.47 (1H, dd, J=9.0, 1.9), 7.51 (4H, m); m/z (ES$^+$) 600 (M+1, 100%).

EXAMPLE 41

(2R,3S,9R)-4-Aza-1,7-dioxa-3-(4-fluorophenyl)-9-methoxy-4-((2-methoxyphenyl)methyl)-9-(2-methoxy-5-(trifluoromethyl)phenyl) spiro[5.4]decane The title compound was prepared from the morpholine of Example 32 according to the method of Example 21 to yield an oil (63 mg, 74%). $^1$H NMR (360 MHz, CDCl$_3$) δ 2.32–2.40 (2H, m), 2.53 (1H, d, J=13.9), 2.86 (1H, br d, J=11.7), 2.97 (3H, s), 3.03 (1H, d, J=13.8), 3.40 (1H, d, J=13.8), 3.46 (1H, s), 3.65 (1H, dd, J=11.4, 2.1), 3.67 (1H, m), 3.69 (3H, s), 3.72 (3H, s), 3.81 (1H, d, J=9.8), 4.27 (1H, dt, J=11.8, 2.1), 4.41 (1H, d, J=9.8), 6.76–6.91 (5H, m), 7.15–7.25 (2H, m), 7.38 (1H, br d, J=6.4), 7.46 (1H, dd, J=8.6, 1.8), 7.50 (~2H, br s); m/z (ES$^+$) 562 (M+1, 100%).

EXAMPLE 42

(2R,3S,9R)-9-Allyloxy-4-aza-4-benzyl-1,7-dioxa-3-(4-fluorophenyl)-9-phenyl-spiro[5.4]decane The title compound was prepared from the alcohol of Example 1 and allyl bromide according to the method of Example 22 to yield an oil (62 mg, 59%). $^1$H NMR (360 MHz, CDCl$_3$) δ 2.24 (1H, d, J=14.2), 2.32 (1H, dt, J=11.8, 3.5), 2.47 (1H, d, J=14.2), 2.78 (1H, d, J=13.3), 2.78 (1H, m), 3.43 (1H, s), 3.61–3.84 (5H, m), 4.23 (1H, dt, J=11.7, 2.5), 4.28 (1H, d, J=9.2), 5.10 (1H, dq, J=10.4, 1.6), 5.28 (1H, dq, J=17.2, 1.7), 5.83–5.93 (1H, m), 6.77–6.81 (2H, m), 6.96 (2H, t, J=8.7), 7.08–7.28 (8H, m), 7.55 (~2H, br s); m/z (ES$^+$) 460 (M+1, 100%).

EXAMPLE 43

(2R,3S,9R)-4-Aza-4-benzyl-1,7-dioxa-3-(4-fluorophenyl)-9-phenyl-9-(phenylmethoxy)spiro[5.4]decane The title compound was prepared from the alcohol of Example 1 and benzyl bromide according to the method of Example 22 to yield an oil which solidified on standing (99 mg, 77%). $^1$H NMR (360 MHz, CDCl$_3$) δ 2.29 (1H, d, J=14.2), 2.35 (1H, dt, J=11.9, 3.3), 2.58 (1H, d, J=14.2), 2.80 (2H, m), 3.45 (1H, s), 3.64 (1H, m), 3.68 (1H, d, J=13.8), 3.79 (1H, d, J=9.3), 4.16 (1H, d, J=11.6), 4.26 (1H, dt, J=11.5, 1.7), 4.33–4.38 (2H, m), 6.85–6.89 (2H, m), 6.95 (2H, t, J=8.6), 7.11–7.32 (13H, m), 7.55 (~2H, br s); m/z (ES$^+$) 510 (M+1, 100%).

EXAMPLE 44

(2R,3S,9R)-4-Aza-1,7-dioxa-3-(4-fluorophenyl)-9-phenyl-9-propyloxy-spiro[5.4]decane The benzylamine of Example 42 was hydrogenated according to the method of Example 9 to yield the title compound as an oil (27 mg, 67%). $^1$H NMR (360 MHz, CDCl$_3$) δ 0.84 (3H, t, J=7.3), 1.54 (2H, sx, J=7.2), 1.84 (~1H, br s), 1.98 (1H, m), 2.15 (1H, d, J=14.1), 2.31 (1H, d, J=13.9), 2.40 (1H, d, J=14.1), 2.94–3.23 (~4H, m), 3.66–3.70 (~1H, m), 3.82 (1H, d, J=9.2), 3.93 (1H, s), 4.18–4.25 (1H, m), 4.29 (1H, d, J=9.1), 6.71–6.92 (~3H, m), 7.04–7.11 (3H, m), 7.20–7.41 (~2H, m); m/z (ES$^+$) 372 (M+1, 100%).

EXAMPLE 45

(2R,3S,9R)-4-Aza-4-benzyl-1,7-dioxa-9-fluoro-3-(4-fluorophenyl)-9-phenyl-spiro[5.4]decane Nitrogen was bubbled through a solution of the alcohol of Example 1 (250 mg, 0.60 mmol) in dichloromethane (6 ml) in a Nalgene™ flask for 5 minutes before cooling to −78° C. Diethylaminosulfur trifluoride (83 μl, 0.63 mmol) was added dropwise and the solution stirred at −78° C. for 4 hours. The reaction mixture was quenched at −78° C. by the addition of water (20 ml), diluted with dichloromethane (20 ml), separated and the organic layer dried (MgSO$_4$) and concentrated to a gum (317 mg). The crude residue was purified by medium pressure silica gel chromatography eluting with 5:1 hexane:ethyl acetate to yield the title compound (~3:1 mixture of diastereomers) as the least polar component as an oil (65 mg, 26%); $^1$H NMR (360 MHz, CDCl$_3$) δ 2.23–2.59 (~3H, m), 2.75–2.92 (~3H, m), 3.50 and 3.54 (1H total, 3:1, 2×s), 3.61–3.78 (~2H, m), 3.98–4.42 (~2H, m), 6.69–7.35 (12H, m), 7.54–7.68 (~2H, br s); $^{13}$C NMR (90.6 MHz, CDCl$_3$, DEPT) δ 24.66 (CH$_2$), 35.83 (CH$_2$), 45.41 and 45.46 (CH$_2$), 46.41, 46.46, 46.53, 46.68 and 46.83 (CH$_2$), 54.69, 55.14, 55.83 and 56.41 (CH$_2$), 66.88, 66.98 and 67.45 (CH), 73.25 and 73.54 (CH$_2$), 75.33 and 75.65 (CH$_2$), 109.65, 109.88 and 110.63 (CH), 118.47, 118.58, 118.99, 119.46 and 119.56 (CH), 120.81, 121.99, 122.03, 122.59, 122.76, 123.16, 123.19, 123.23, 123.30, 123.80, 123.83 and 123.92 (CH), 127.01, 127.09, 127.27 and 127.36 (CH), 134.90 (CH); m/z (ES$^+$) 422 (M+1, 100%), 402 (M−19, 28).

EXAMPLE 46

(2R,3S,9R)-4-Aza-1,7-dioxa-9-fluoro-3-(4-fluorophenyl)-9-phenyl-spiro[5.4]decane The benzylamine of Example 45 was hydrogenated according to the method of Example 9 to yield the title compound as an oil (18 mg, 46%); m/z (ES$^+$) 332 (M+1, 18%), 102 (100).

EXAMPLE 47

(2R,3S,9R)-4-Aza-4-benzyl-1,7-dioxa-3-(4-fluorophenyl)-9-hydroxy-9-(2-(hydroxymethyl)phenyl)spiro[5.4]decane The product of Description 12 (350 mg) was heated at reflux in a solution of 0.01 HCl (2 ml) and water:ethanol (10 ml, 1:1). The ethanol was removed by distillation and the aqueous residue basified (NaHCO$_3$) and extracted with ethyl acetate (3×30 ml). The combined organic extracts were washed with water and saturated brine (1×30 ml each), dried (MgSO$_4$) and concentrated to a crude oil which was purified by flash silica gel chromatography eluting with 9:1 to 4:1 hexane:ethyl acetate to yield the title compound as an oil (136 mg, 52%). m/z (ES$^+$) 450 (M+1, 100%).

EXAMPLE 48

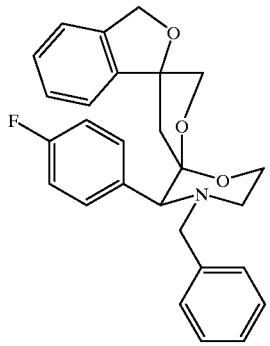

[2'R-[2'α(S*),4'α]]-3"-(4-fluorophenyl)-4"-(phenylmethyl)dispiro-[isobenzofuran-1(3H),4'(5'H)-furan-2'(3H),2"-morpholine]

Methanesulfonylchloride (23 μl, 0.29 mmol) was added to a solution of the diol of Example 47 (130 mg, 0.29 mmol) and triethylamine (81 μl, 0.58 mmol) in dichloromethane (5 ml) cooled to 0° C. The resulting mixture was allowed to warm to 20° C. and stirred for 18 hours. The reaction mixture was washed sequentially with 1.0M citric acid, water and saturated brine, dried (MgSO$_4$) and concentrated to a yellow oil which was purified by flash silica gel chromatography eluting with 19:1 to 4:1 hexane:ethyl acetate to yield the title compound as white foam (90 mg, 72%). $^1$H NMR (360 MHz, CDCl$_3$) δ 2.12 (1H, d, J=14.2), 2.28–2.36 (1H, m), 2.37 (1H, d, J=14.2), 2.82 (1H, d, J=12.7), 2.77–2.88 (1H, m), 3.50 (1H, s), 3.62–3.76 (3H, m), 4.24 (1H, d, J=9.7), 4.20–4.30 (1H, m), 5.03 (2H, s), 6.09 (1H, d, J=7.4), 7.02–7.30 (10H, m), 7.65 (2H, br s); m/z (ES$^+$) 432 (M+1, 100%).

EXAMPLE 49

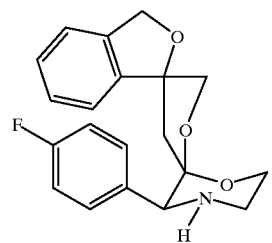

[2'R-[2'α(S*),4'α]]-3"-(4-fluorophenyl)dispiro[isobenzofuran-1(3H),4'(5'H)-furan-2'(3H),2"-morpholine]

The benzylamine of Example 48 was hydrogenated according to the method of Example 9 to yield the title compound as a foam (15 mg, 38%). $^1$H NMR (360 MHz, CDCl$_3$) δ 2.02 (1H, d, J=14.2), 2.23 (1H, d, J=14.2), 3.05 (1H, dd, J=9.5, 2.7), 3.21 (1H, td, J=12.3, 3.6), 3.77 (1H, d, J=9.8), 3.74–3.82 (1H, m), 4.01 (1H, s), 4.28 (1H, d, J=9.8), 4.25–4.33 (1H, m), 5.04 (2H, s), 6.19 (1H, d, J=7.5), 7.02–7.13 (4H, m), 7.17 (1H, d, J=6.6), 7.48–7.54 (2H, m); m/z (ES$^+$) 342 (M+1, 100%).

What is claimed is:

1. A compound of the formula (I):

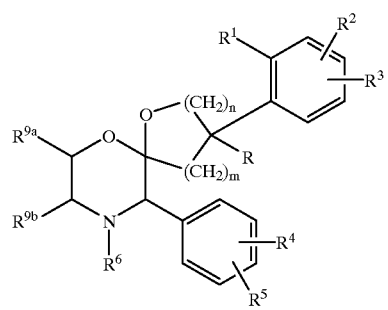

wherein

R represents hydroxy, C$_{1-6}$alkoxy, C$_{3-6}$alkenyloxy, C$_{3-6}$alkynyloxy, fluoroC$_{1-6}$alkoxy, C$_{3-7}$cycloalkoxy, C$_{3-7}$cycloalkylC$_{1-4}$alkoxy, phenoxy, benzyloxy or halogen, wherein the phenyl moiety of said phenoxy or benzyloxy is optionally substituted by one, two or three substituents selected from C$_{1-6}$alkyl, C$_{1-6}$alkoxy, halogen and trifluoromethyl;

$R^1$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, fluoro$C_{1-6}$alkyl, fluoro$C_{1-6}$alkoxy, $C_{1-4}$alkyl wherein the $C_{1-4}$alkyl is substituted by a $C_{1-4}$alkoxy group or a hydroxy group, hydroxy, trimethylsilyl, nitro, CN, $SR^a$, $SOR^a$, $SO_2R^a$, $COR^a$, $CO_2R^a$, $CONR^aR^b$, $NR^aR^b$, $SO_2NR^aR^b$, or $OC_{1-4}$alkyl$NR^aR^b$, where $R^a$ and $R^b$ are each independently hydrogen or $C_{1-4}$alkyl;

$R^2$ and $R^3$ each independently represent hydrogen, halogen, $C_{1-6}$alkyl, $C_{1-6}$alkoxy substituted by $C_{1-4}$alkoxy or trifluoromethyl;

or R and $R^1$ may be joined such that —R—$R^1$— is a linkage selected from —O—CH$_2$— and —O—CH$_2$CH$_2$—;

or, where $R^1$ and $R^2$ are attached to adjacent carbon atoms, they may be joined together such that —$R^1$—$R^2$— is a linkage selected from —OCH$_2$CH$_2$CH$_2$—, —OCH$_2$CH$_2$O—, —OCH$_2$CH$_2$—, —OCH$_2$O—, —NR$^a$CH$_2$CH$_2$CH$_2$—, —NR$^a$CH$_2$CH$_2$—, —CH$_2$CH$_2$CH$_2$CH$_2$—, —CH$_2$CH$_2$CH$_2$—, —CH=CH—CH=CH—, —O—CH=CH—, —NR$^a$—CH=CH—, —S—CH=CH—, —NR$^a$—CH=N—, —O—CH=N—, —S—CH=N—, —N=CH—CH=CH—, and —CH=N—CH=CH—, where $R^a$ is as previously defined;

$R^4$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, $C_{1-4}$alkyl wherein the $C_{1-4}$alkyl is substituted by a $C_{1-4}$alkoxy group, trifluoromethyl, nitro, CN, $SR^a$, $SOR^a$, $SO_2R^a$, $COR^a$, $CO_2R^a$, $CONR^aR^b$ where $R^a$ and $R^b$ are as previously defined;

$R^5$ represents hydrogen, halogen, $C_{1-6}$alkyl, $C_{1-6}$alkoxy substituted by $C_{1-4}$alkoxy or trifluoromethyl;

$R^6$ represents hydrogen, $COR^a$, $CO_2R^a$, $COCONR^aR^b$, $COCO_2R^a$, $C_{1-6}$alkyl optionally substituted by one group selected from ($CO_2R^a$, $CONR^aR^b$, hydroxy, CN, $COR^a$, $NR^aR^b$, $C(NOH)NR^aR^b$, CONHphenyl ($C_{1-4}$alkyl), $COCO_2R^a$, $CONHNR^aR^b$, $C(S)NR^aR^b$, $CONR^aC_{1-6}$alkyl$R^{12}$; $CONR^{13}C_{2-6}$alkenyl, $CONR^{13}C_{2-6}$alkynyl, $COCONR^aR^b$, $CONR^aC(NR^b)NR^aR^b$, $CONR^a$heteroaryl, wherein the heteroaryl is selected from:

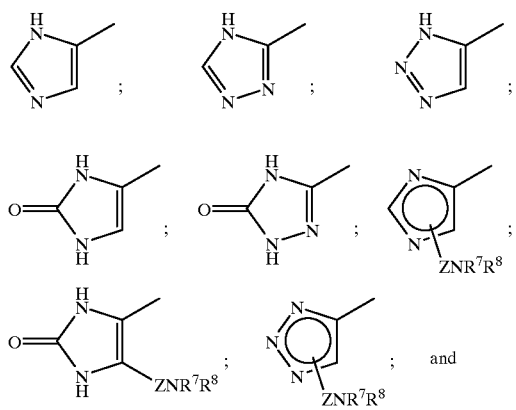

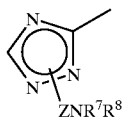

and phenyl optionally substituted by one, two or three substituents selected from $C_{1-6}$alkyl, $C_{1-6}$alkoxy, halogen and trifluoromethyl);

or $R^6$ represents a group of the formula —CH$_2$C≡CCH$_2$NR$^7$R$^8$ where $R^7$ and $R^8$ are as defined below;

or $R^6$ represents $C_{1-6}$alkyl, optionally substituted with an oxo, substituted by a 5-membered or 6-membered heterocyclic ring containing 2 or 3 nitrogen atoms optionally substituted by =O or =S and optionally substituted by a group of the formula ZNR$^7$R$^8$ where Z is $C_{1-6}$alkylene or $C_{3-6}$cycloalkyl;

$R^7$ is $C_{1-4}$alkyl or $C_{2-4}$alkyl which is substituted by hydroxyl or $C_{1-2}$alkoxy;

$R^8$ is $C_{1-4}$alkyl or $C_{1-4}$alkyl substituted by a hydroxyl or $C_{1-2}$alkoxy;

or $R^7$ and $R^8$ may be linked so that, together with the nitrogen atom to which they are attached, they form an azetidinyl, pyrrolidinyl, piperidyl, morpholino, thiomorpholino, or piperazino group which is substituted on the nitrogen atom by $C_{1-4}$alkyl or $C_{2-4}$alkyl substituted by hydroxy or $C_{1-2}$alkoxy;

$R^{9a}$ and $R^{9b}$ each independently represent hydrogen or $C_{1-4}$alkyl, or $R^{9a}$ and $R^{9b}$ are joined so, together with the carbon atoms to which they are attached, there is formed a $C_{5-7}$ ring;

$R^{12}$ represents, $OR^a$, $CONR^aR^b$ or heteroaryl;

$R^{13}$ represents H or $C_{1-6}$alkyl;

m is 1 or 2; and n is 1;

or a pharmaceutically acceptable salt thereof.

2. A compound as claimed in claim 1 wherein R represents hydroxy, $C_{1-3}$alkoxy, $C_{3-5}$alkenyloxy, phenoxy or halogen.

3. A compound as claimed in claim 1 wherein $R^1$ represents hydrogen, halogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, $C_{1-6}$alkoxy, $C_{1-4}$alkyl substituted by a $C_{1-4}$alkoxy group, $OCF_3$, hydroxy, trifluoromethyl, trimethylsilyl, nitro, CN, $SR^a$, $SOR^a$, $SO_2R^a$, $COR^a$, $CO_2R^a$, $CONR^aR^b$ where $R^a$ and $R^b$ are each independently hydrogen or $C_{1-4}$alkyl; and $R^2$ and $R^3$ each independently represent hydrogen, halogen, $C_{1-6}$alkyl, $C_{1-6}$alkoxy substituted by $C_{1-4}$alkoxy or trifluoromethyl.

4. A compound as claimed in claim 1 wherein $R^1$ is hydrogen, $C_{1-4}$alkyl, $C_{1-4}$alkoxy, halogen, fluoro$C_{1-3}$alkyl or fluoro$C_{1-3}$alkoxy.

5. A compound as claimed in claim 1 wherein $R^2$ is hydrogen, $C_{1-4}$alkyl, $C_{1-4}$alkoxy, halogen or $CF_3$.

6. A compound as claimed in claim 1 wherein $R^3$ is hydrogen, fluorine, chlorine or $CF_3$.

7. A compound as claimed in claim 1 wherein $R^4$ is hydrogen.

8. A compound as claimed in claim 1 wherein $R^5$ is hydrogen, fluorine, chlorine or $CF_3$.

9. A compound as claimed in claim 1 wherein $R^{9a}$ and $R^{9b}$ are each independently hydrogen or methyl.

10. A compound of formula (Ia)

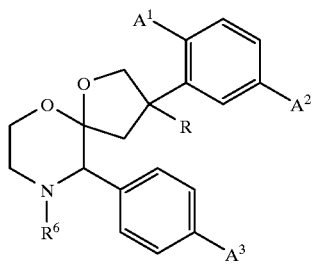

(Ia)

wherein R and R⁶ are as defined in claim 1;
A¹ is hydrogen, $C_{1-3}$alkyl, $C_{1-3}$alkoxy, halogen, fluoro$C_{1-3}$alkyl or fluoro$C_{1-3}$alkoxy;
A² is hydrogen, halogen, $C_{1-4}$alkyl or trifluoromethyl; and
A³ is hydrogen or halogen;
or a pharmaceutically acceptable salt thereof.

11. A compound as claimed in claim 10 wherein R⁶ is hydrogen, $C_{1-3}$alkyl substituted by phenyl wherein said phenyl ring is optionally substituted by $C_{1-3}$alkoxy or $CF_3$, or R⁶ is a group of formula —CH₂C≡CCH₂NR⁷R⁸, or R⁶ is $C_{1-3}$alkyl substituted by a 5-membered heterocyclic ring selected from:

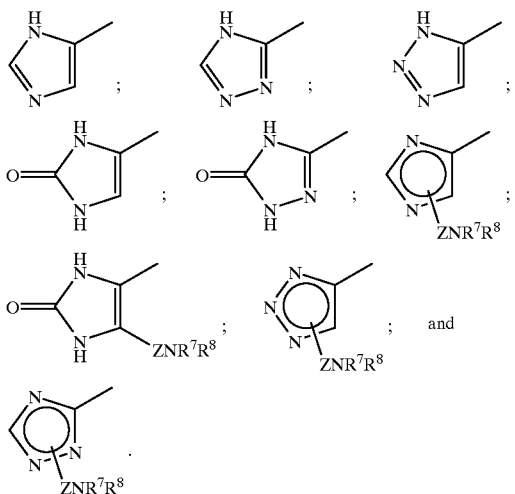

12. A compound selected from:
(2R,3S,9R)-4-aza-4-benzyl-1,7-dioxa-3-(4-fluorophenyl)-9-hydroxy-9-phenyl-spiro[5.4]decane;
(2R,3S,9R)-4-aza-4-benzyl-1,7-dioxa-3-(4-fluorophenyl)-9-hydroxy-9-(2-methoxyphenyl)spiro[5.4]decane;
(2R,3S,9R)-4-aza-4-benzyl-1,7-dioxa-3-(4-fluorophenyl)-9-hydroxy-9-(2-(trifluoromethyl)phenyl)spiro[5.4]decane;
(2R,3S,9R)-4-aza-4-benzyl-1,7-dioxa-3-(4-fluorophenyl)-9-hydroxy-9-(2-methoxy-5-(trifluoromethyl)phenyl)spiro[5.4]decane;
(2R,3S,9R)-4-aza-4-benzyl-1,7-dioxa-3-(4-fluorophenyl)-9-hydroxy-9-(2-methoxy-5-(trifluoromethyl)phenyl)spiro[5.4]decane;
(2R,3S,9R)-4-aza-4-benzyl-1,7-dioxa-3-(4-fluorophenyl)-9-hydroxy-9-(2-(trifluoromethoxy)phenyl)spiro[5.4]decane;
(+/−)-(2R*,3S*,9R*)-4-aza-4-benzyl-1,7-dioxa-3-(4-fluorophenyl)-9-hydroxy-9-(2-methylphenyl)spiro[5.4]decane;
(2R,3S,9R)-4-aza-4-benzyl-1,7-dioxa-9-(2-ethylphenyl)-3-(4-fluorophenyl)-9-hydroxy-spiro[5.4]decane;
(2R,3S,9R)-4-aza-4-benzyl-9-(2-chlorophenyl)-1,7-dioxa-3-(4-fluorophenyl)-9-hydroxy-spiro[5.4]decane;
(2R,3S,9R)-4-aza-1,7-dioxa-3-(4-fluorophenyl)-9-hydroxy-9-phenylspiro[5.4]decane;
(2R,3S,9R)-4-aza-1,7-dioxa-3-(4-fluorophenyl)-9-hydroxy-9-(2-methoxyphenyl)spiro[5.4]decane;
(2R,3S,9R)-4-aza-1,7-dioxa-3-(4-fluorophenyl)-9-hydroxy-9-(2-(trifluoromethyl)phenyl)spiro[5.4]decane;
(2R,3S,9R)-4-aza-1,7-dioxa-3-(4-fluorophenyl)-9-hydroxy-9-(2-methoxy-5-(trifluoromethyl)phenyl)spiro[5.4]decane;
(2R,3S,9R)-4-aza-1,7-dioxa-3-(4-fluorophenyl)-9-hydroxy-9-(2-methoxy-5-(trifluoromethyl)phenyl)spiro[5.4]decane;
(2R,3S,9R)-4-aza-1,7-dioxa-3-(4-fluorophenyl)-9-hydroxy-9-(2-(trifluoromethoxy)phenyl)spiro[5.4]decane;
(+/−)-(2R*,3S*,9R*)-4-aza-1,7-dioxa-3-(4-fluorophenyl)-9-hydroxy-9-(2-methylphenyl)spiro[5.4]decane;
(2R,3S,9R)-4-aza-4-(2,3-dihydro-3-oxo-1,2,4-triazol-5-yl)methyl-1,7-dioxa-3-(4-fluorophenyl)-9-hydroxy-9-(2-methoxyphenyl)spiro[5.4]decane;
(2R,3S,9R)-4-aza-4-(2,3-dihydro-3-oxo-1,2,4-triazol-5-yl)methyl-1,7-dioxa-3-(4-fluorophenyl)-9-hydroxy-9-(2-trifluoromethyl)phenyl)-spiro[5.4]decane;
(2R,3S,9R)-4-aza-4-(4-(N,N-dimethylamino)-but-2-ynyl)-1,7-dioxa-3-(4-fluorophenyl)-9-hydroxy-9-(2-methoxy-5-(trifluoromethyl)phenyl)spiro[5.4]decane;
(2R,3S,9R)-4-aza-4-(5-(N,N-dimethylaminomethyl)-1,2,3-triazol-4-yl)methyl-1,7-dioxa-3-(4-fluorophenyl)-9-hydroxy-9-(2-methoxy-5-(trifluoromethyl)phenyl)spiro[5.4]decane;
(2R,3S,9R)-4-aza-1,7-dioxa-3-(4-fluorophenyl)-9-hydroxy-4-(1(S)-phenylethyl)-9-(2-(trifluoromethyl)phenyl)spiro[5.4]decane;
(2R,3S,9R)-4-aza-1,7-dioxa-3-(4-fluorophenyl)-9-hydroxy-4-(1(R)-phenylethyl)-9-(2-(trifluoromethyl)phenyl)spiro[5.4]decane;
(2R,3S,9R)-4-aza-1,7-dioxa-3-(4-fluorophenyl)-9-hydroxy-4-((2-(trifluoromethyl)phenyl)methyl)-9-(2-(trifluoromethyl)phenyl)spiro[5.4]decane;
(+/−)-(2R*,3S*,9R*)-4-aza-4-benzyl-1,7-dioxa-3-(4-fluorophenyl)-9-methoxy-9-phenyl-spiro[5.4]decane;
(2R,3S,9R)-4-aza-4-benzyl-1,7-dioxa-3-(4-fluorophenyl)-9-methoxy-9-(2-methoxyphenyl)spiro[5.4]decane;
(2R,3S,9R)-4-aza-4-benzyl-1,7-dioxa-3-(4-fluorophenyl)-9-methoxy-9-(2-(trifluoromethyl)phenyl)spiro[5.4]decane;
(2R,3S,9R)-4-aza-4-benzyl-1,7-dioxa-3-(4-fluorophenyl)-9-methoxy-9-(2-methoxy-5-(trifluoromethyl)phenyl)spiro[5.4]decane;
(+/−)-(2R*,3S*,9R*)-4-aza-4-benzyl-1,7-dioxa-3-(4-fluorophenyl)-9-methoxy-9-(2-methylphenyl)spiro[5.4]decane;
(2R,3S,9R)-4-aza-4-benzyl-1,7-dioxa-9-(2-ethylphenyl)-3-(4-fluorophenyl)-9-methoxy-spiro[5.4]decane;

(2R,3S,9R)-4-aza-4-benzyl-9-(2-chlorophenyl)-1,7-dioxa-3-(4-fluorophenyl)-9-methoxy-spiro[5.4]decane;

(+/−)-(2R*,3S*,9R*)-4-aza-1,7-dioxa-3-(4-fluorophenyl)-9-methoxy-9-phenyl-spiro[5.4]decane;

(2R,3S,9R)-4-aza-1,7-dioxa-3-(4-fluorophenyl)-9-methoxy-9-(2-methoxyphenyl)spiro[5.4]decane;

(2R,3S,9R)-4-aza-1,7-dioxa-3-(4-fluorophenyl)-9-methoxy-9-(2-trifluoromethyl)phenyl)spiro[5.4]decane;

(2R,3S,9R)-4-aza-4-1,7-dioxa-3-(4-fluorophenyl)-9-methoxy-9-(2-methoxy-5-(trifluoromethyl)phenyl)spiro[5.4]decane;

(2R,3S,9R)-4-aza-1,7-dioxa-3-(4-fluorophenyl)-9-methoxy-9-(2-methylphenyl)spiro[5.4]decane;

(2R,3S,9R)-4-aza-1,7-dioxa-9-(2-ethylphenyl)-3-(4-fluorophenyl)-9-methoxy-spiro[5.4]decane;

(2R,3S,9R)-4-aza-4-(5-(N,N-dimethylaminomethyl)-1,2,3-triazol-4-yl)methyl-1,7-dioxa-3-(4-fluorophenyl)-9-methoxy-9-(2-methoxy-5-(trifluoromethyl)phenyl)spiro[5.4]decane;

(2R,3S,9R)-4-aza-4-(5-(N,N-dimethylaminomethyl)-1,2,3-tetrazol-4-yl)methyl-1,7-dioxa-3-(4-fluorophenyl)-9-methoxy-9-(2-(trifluoromethyl)phenyl)spiro[5.4]decane;

(2R,3S,9R)-4-aza-1,7-dioxa-3-(4-fluorophenyl)-9-methoxy-4-(1-(S)-phenylethyl)-9-(2-methoxy-5-(trifluoromethyl)phenyl)spiro[5.4]decane;

(2R,3S,9R)-4-aza-1,7-dioxa-3-(4-fluorophenyl)-9-methoxy-4-(1-(R)-phenylethyl)-9-(2-methoxy-5-(trifluoromethyl)phenyl)spiro[5.4]decane;

(2R,3S,9R)-4-aza-1,7-dioxa-3-(4-fluorophenyl)-9-methoxy-9-(2-methoxy-5-(trifluoromethyl)phenyl)-4-((2-(trifluoromethyl)phenyl)methyl)spiro[5.4]decane;

(2R,3S,9R)-4-aza-1,7-dioxa-3-(4-fluorophenyl)-9-methoxy-9-(2-methoxy-5-(trifluoromethyl)phenyl)-4-((3-(trifluoromethyl)phenyl)methyl)spiro[5.4]decane;

(2R,3S,9R)-4-aza-1,7-dioxa-3-(4-fluorophenyl)-9-methoxy-9-(2-methoxy-5-(trifluoromethyl)phenyl)-4-((4-(trifluoromethyl)phenyl)methyl)spiro[5.4]decane;

(2R,3S,9R)-4-aza-1,7-dioxa-3-(4-fluorophenyl)-9-methoxy-4-((2-methoxyphenyl)methyl)-9-(2-methoxy-5-(trifluoromethyl)phenyl)spiro[5.4]decane;

(2R,3S,9R)-9-allyloxy-4-aza-4-benzyl-1,7-dioxa-3-(4-fluorophenyl)-9-phenyl-spiro[5.4]decane;

(2R,3S,9R)-4-aza-4-benzyl-1,7-dioxa-3-(4-fluorophenyl)-9-phenyl-9-(phenylmethyloxy)spiro[5.4]decane;

(2R,3S,9R)-4-aza-1,7-dioxa-3-(4-fluorophenyl)-9-phenyl-9-propyloxy-spiro[5.4]decane;

(2R,3S,9R)-4-aza-4-benzyl-1,7-dioxa-9-fluoro-3-(4-fluorophenyl)-9-phenyl-spiro[5.4]decane;

(2R,3S,9R)-4-aza-1,7-dioxa-9-fluoro-3-(4-fluorophenyl)-9-phenylspiro[5.4]decane;

(2R,3S,9R)-4-aza-4-benzyl-1,7-dioxa-3-(4-fluorophenyl)-9-hydroxy-9-(2-(hydroxymethyl)phenyl)spiro[5.4]decane;

[2'R-[2'α(S*),4'α]]-3"-(4-fluorophenyl)-4"-(phenylmethyl)dispiro[isobenzofuran-1(3H),4'(5'H)-furan-2'(3H),2"-morpholine];

[2'R-[2'α(S*),4'α]]-3"-(4-fluorophenyl)dispiro[isobenzofuran-1(3H),4'(5'H)-furan-2'(3H),2"-morpholine];

or a pharmaceutically acceptable salt thereof.

13. A pharmaceutical composition comprising a compound as claimed in claim 1 in association with a pharmaceutically acceptable carrier or excipient.

14. A method for the treatment of physiological disorders associated with an excess of tachykinins, which method comprises administration to a patient in need thereof of a tachykinin reducing amount of a compound according to claim 1.

15. A method according to claim 14 for the treatment of pain or inflammation.

16. A method according to claim 14 for the treatment of migraine.

17. A method according to claim 14 for the treatment of emesis.

18. A method according to claim 14 for the treatment of postherpetic neuralgia.

* * * * *